(12) United States Patent
Seifert et al.

(10) Patent No.: US 7,158,838 B2
(45) Date of Patent: Jan. 2, 2007

(54) ARRANGEMENT FOR IMPLANTING A MINIATURIZED CARDIAC LEAD HAVING A FIXATION HELIX

(75) Inventors: Kevin R. Seifert, Forest Lake, MN (US); Travis S. Lee, Lake Elmo, MN (US); Laurie D. Foerster, Mound, MN (US)

(73) Assignee: Medtronic, Inc., Minneapolis, MN (US)

( * ) Notice: Subject to any disclaimer, the term of this patent is extended or adjusted under 35 U.S.C. 154(b) by 594 days.

(21) Appl. No.: 10/356,143

(22) Filed: Jan. 31, 2003

(65) Prior Publication Data

US 2004/0172116 A1    Sep. 2, 2004

(51) Int. Cl.
    *A61N 1/05*    (2006.01)
(52) U.S. Cl. .................. 607/127; 604/528; 606/129
(58) Field of Classification Search ............. 607/116,
                607/119, 126, 127, 131; 606/129; 600/375;
                                                                604/523–539
    See application file for complete search history.

(56) References Cited

U.S. PATENT DOCUMENTS

| 3,835,864 | A |  | 9/1974  | Rasor et al. |
| 4,233,992 | A |  | 11/1980 | Bisping |
| 5,003,990 | A |  | 4/1991  | Osypka |
| 5,056,516 | A |  | 10/1991 | Spehr ................. 128/419 P |
| 5,246,014 | A |  | 9/1993  | Williams et al. |
| 5,304,218 | A |  | 4/1994  | Alferness |
| 5,851,226 | A | * | 12/1998 | Skubitz et al. ............. 607/126 |
| 5,897,584 | A |  | 4/1999  | Herman |
| 5,902,331 | A |  | 5/1999  | Bonner et al. |
| 6,033,414 | A |  | 3/2000  | Tockman et al. ........... 606/129 |
| 6,132,390 | A |  | 10/2000 | Cookston et al. ........... 600/585 |
| 6,132,456 | A |  | 10/2000 | Sommer et al. |
| 6,185,464 | B1 |  | 2/2001  | Bonner et al. |
| 6,269,272 | B1 | * | 7/2001  | Fischer, Sr. ................. 607/127 |
| 6,408,214 | B1 |  | 6/2002  | Williams et al. |
| 6,478,777 | B1 |  | 11/2002 | Honeck et al. ........ 604/164.01 |

* cited by examiner

*Primary Examiner*—George R. Evanisko
*Assistant Examiner*—Michael Kahelin
(74) *Attorney, Agent, or Firm*—Michael C. Soldner; Carol F. Barry; Girma Wolde-Michael

(57) ABSTRACT

An introducer system and method for positioning and fixedly engaging a lead at an implantation site that includes a torque transfer sheath, extending from a proximal end to a distal end, receiving the lead, an outer sheath, having a distal end, receiving the lead positioned within the torque transfer sheath, and a handle operable between a first position enabling advancement and retraction of the lead through the handle and a second position fixedly engaging a proximal end of the lead within the handle. The lead is advanced through the outer sheath to extend outward a predetermined distance from the distal end of the outer sheath and the fixation helix is rotated through the predetermined distance to be fixedly engaged at the implantation site in response to simultaneous rotation and advancement of the lead and the torque transfer sheath through rotation and advancement of the handle in the second position.

18 Claims, 17 Drawing Sheets

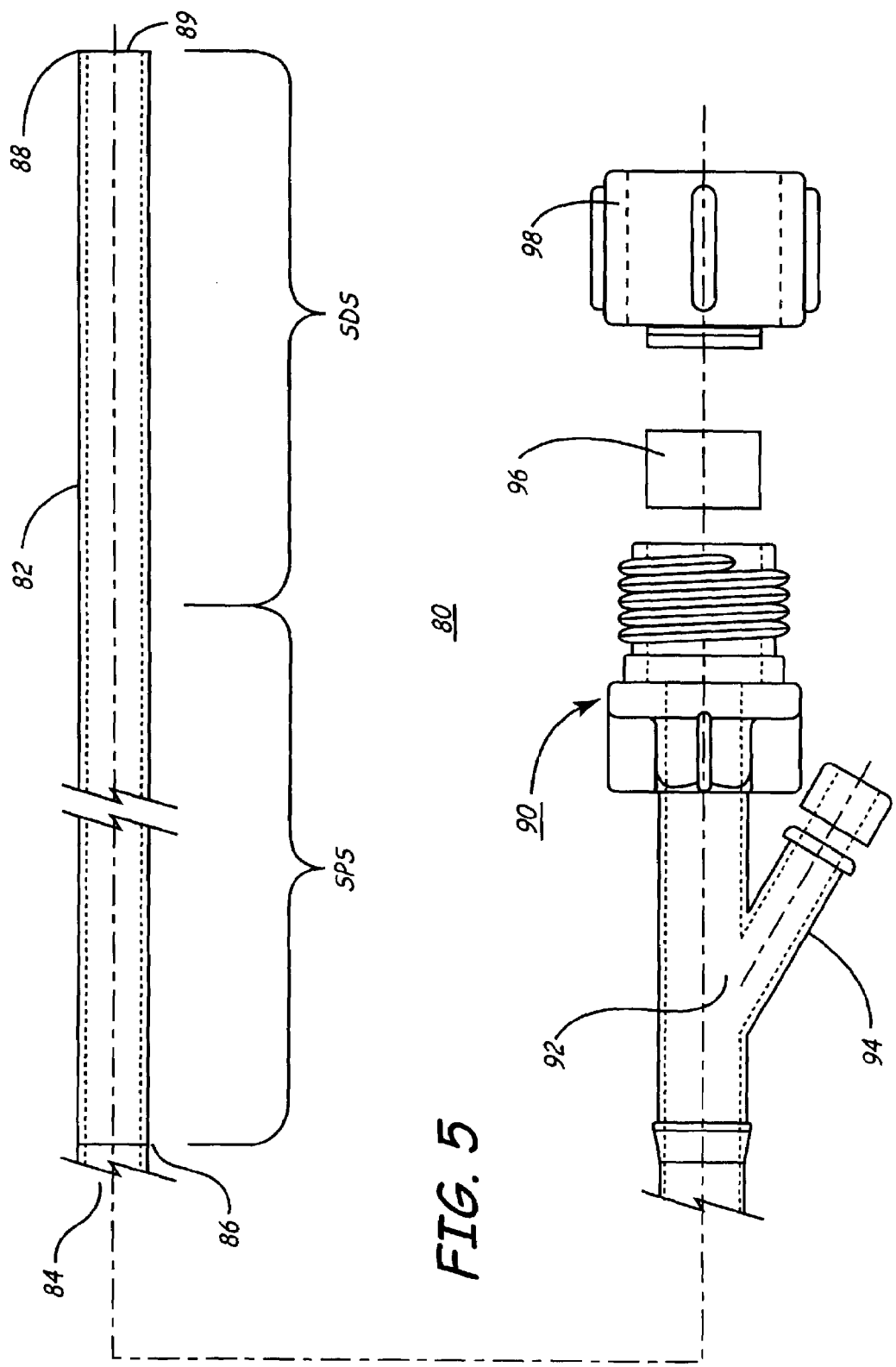

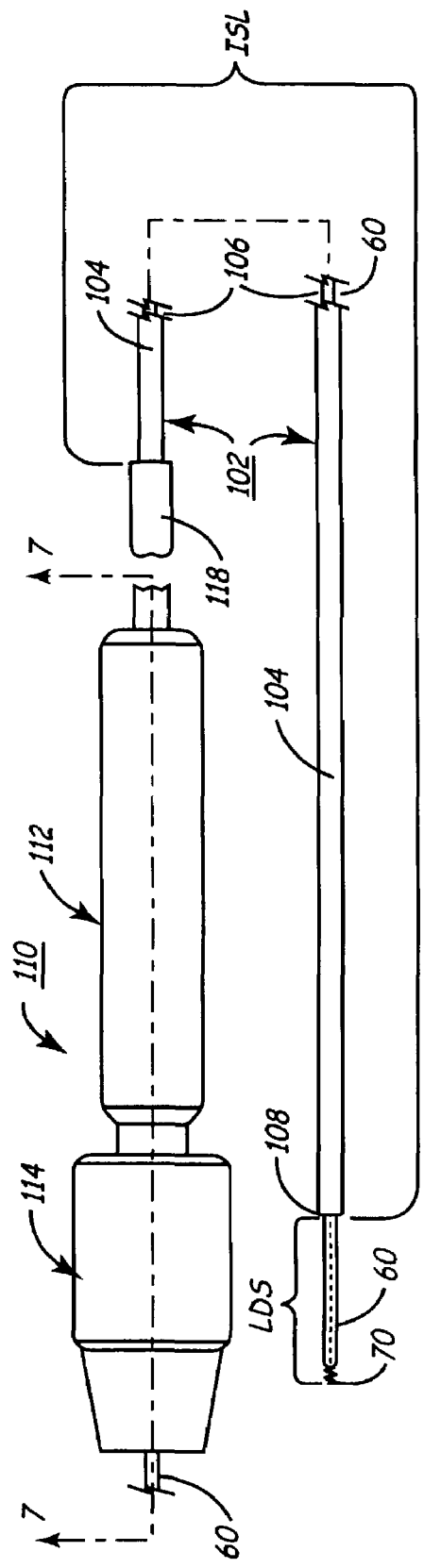
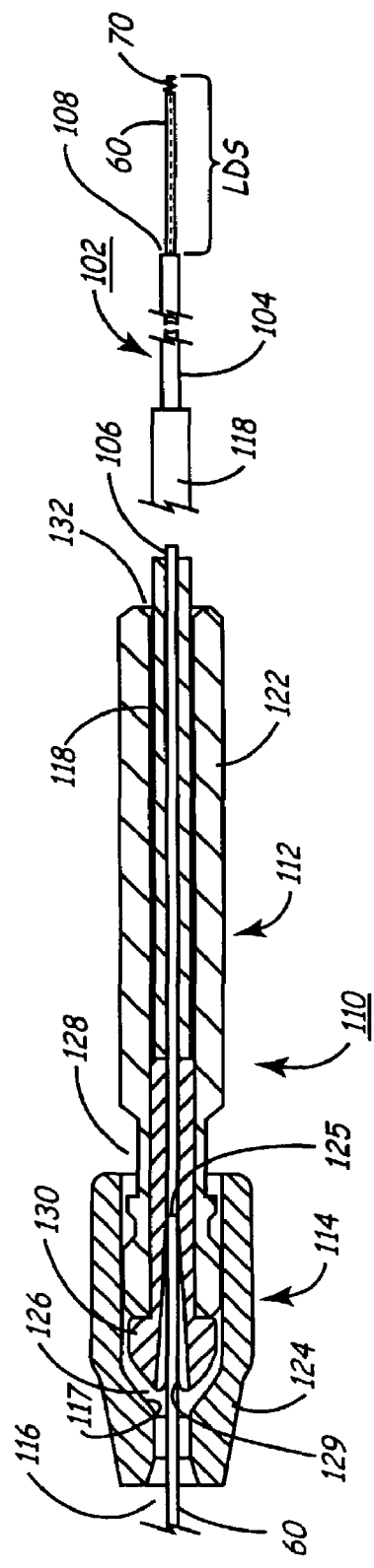

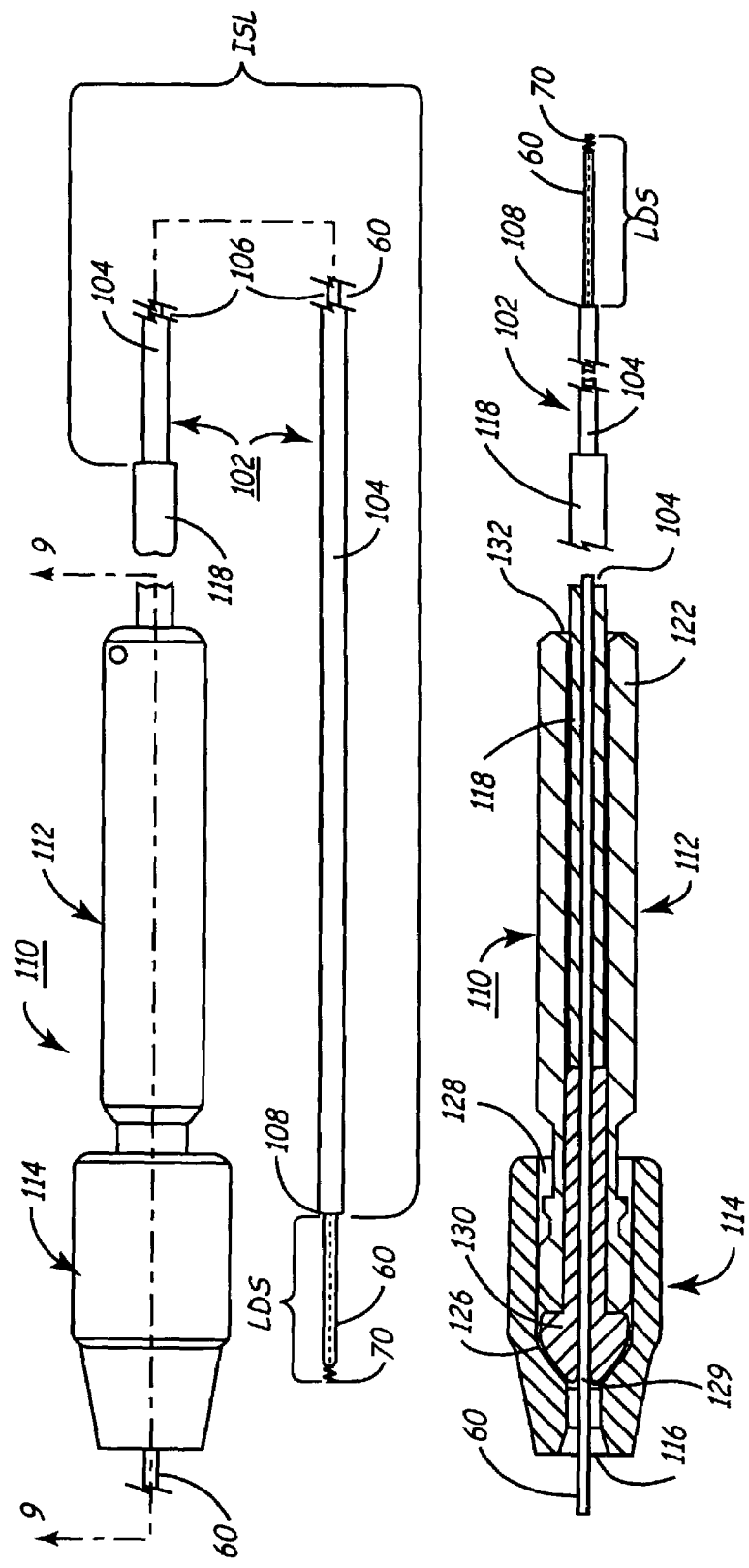

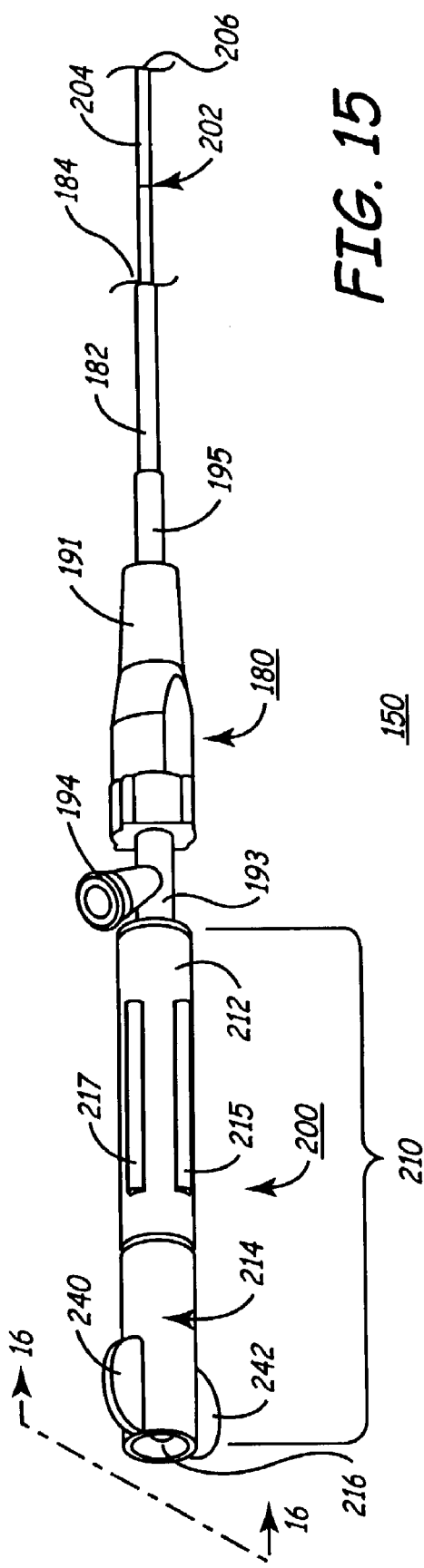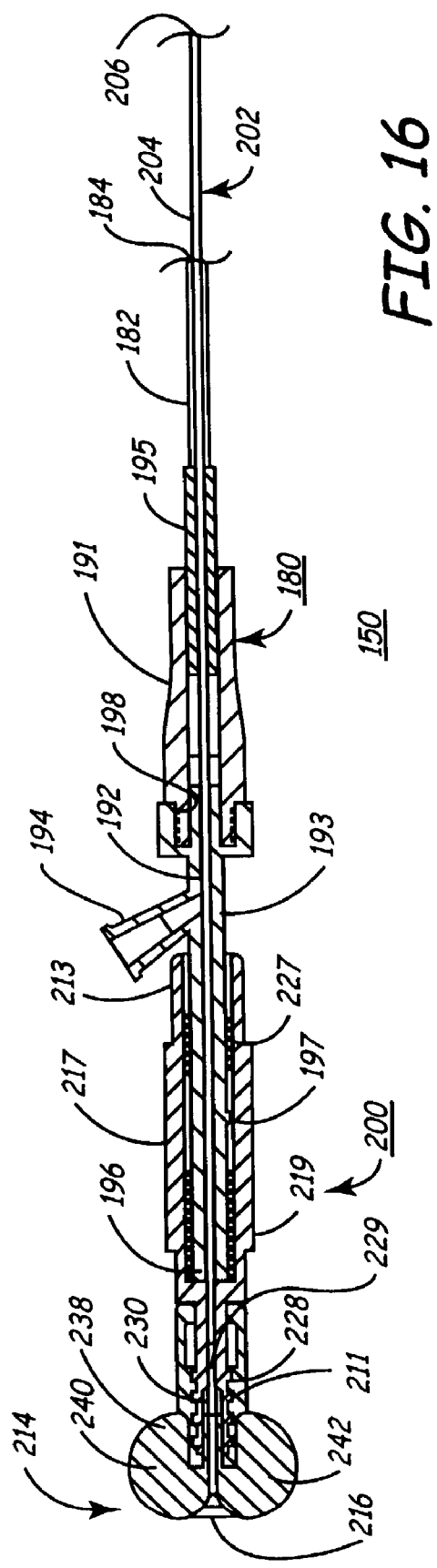

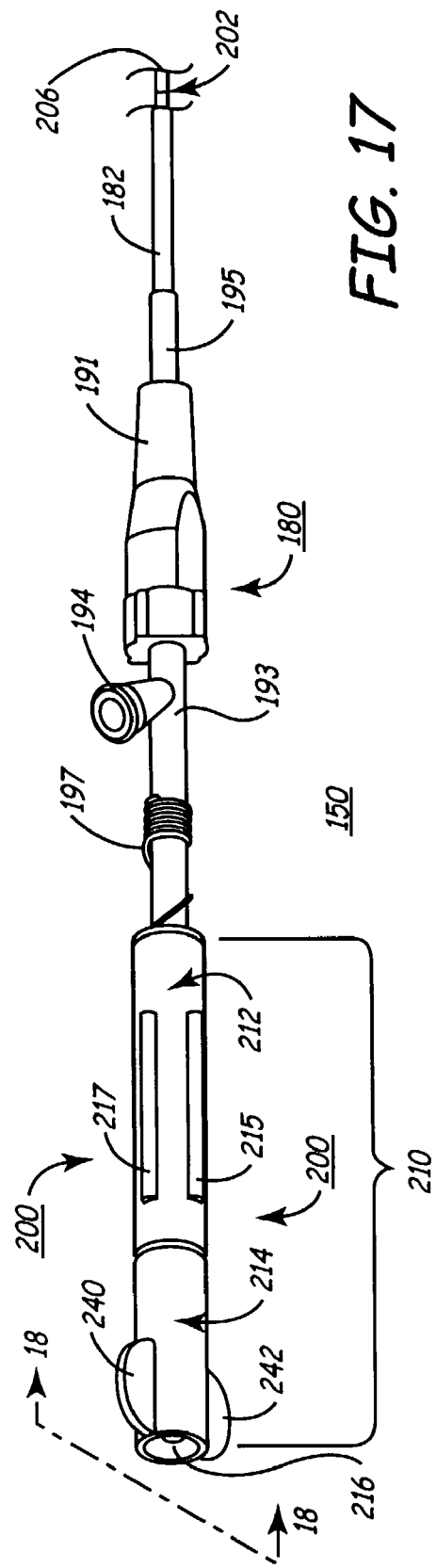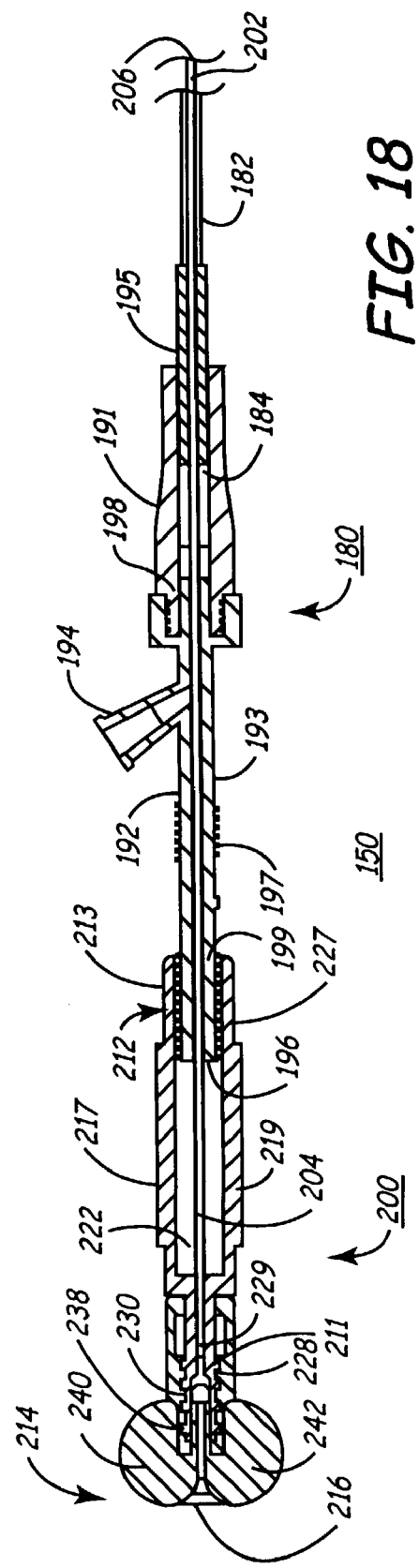

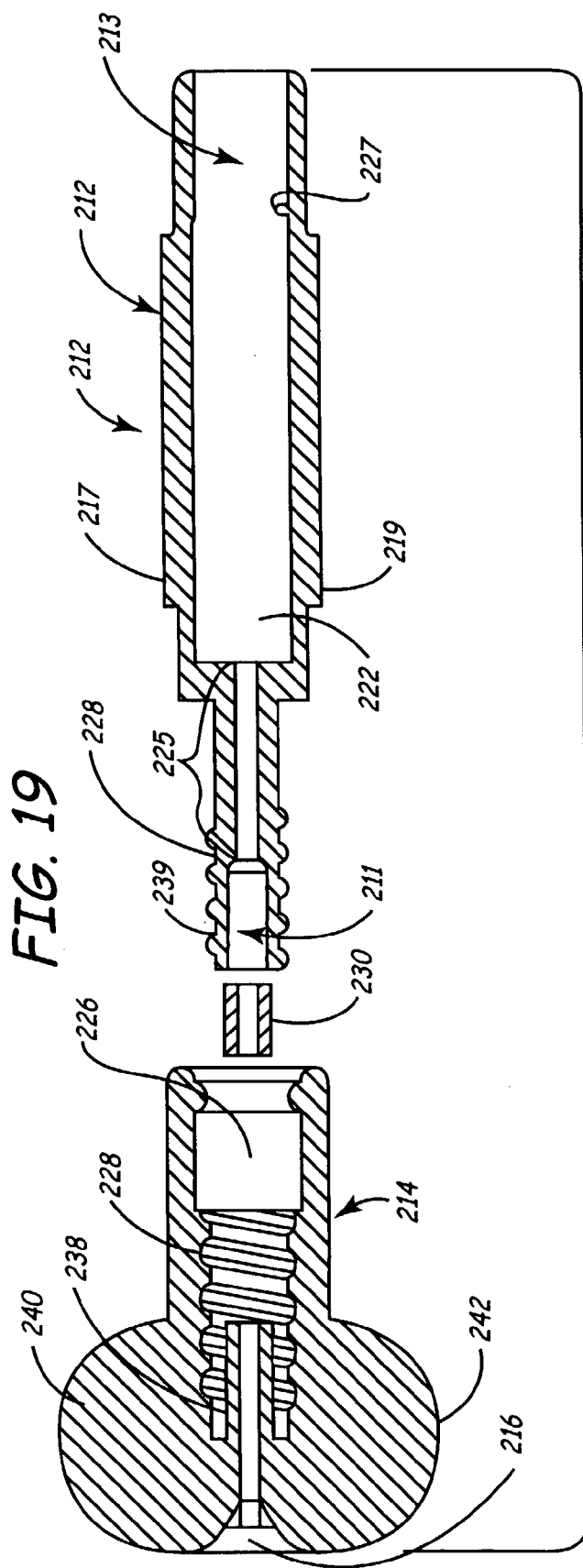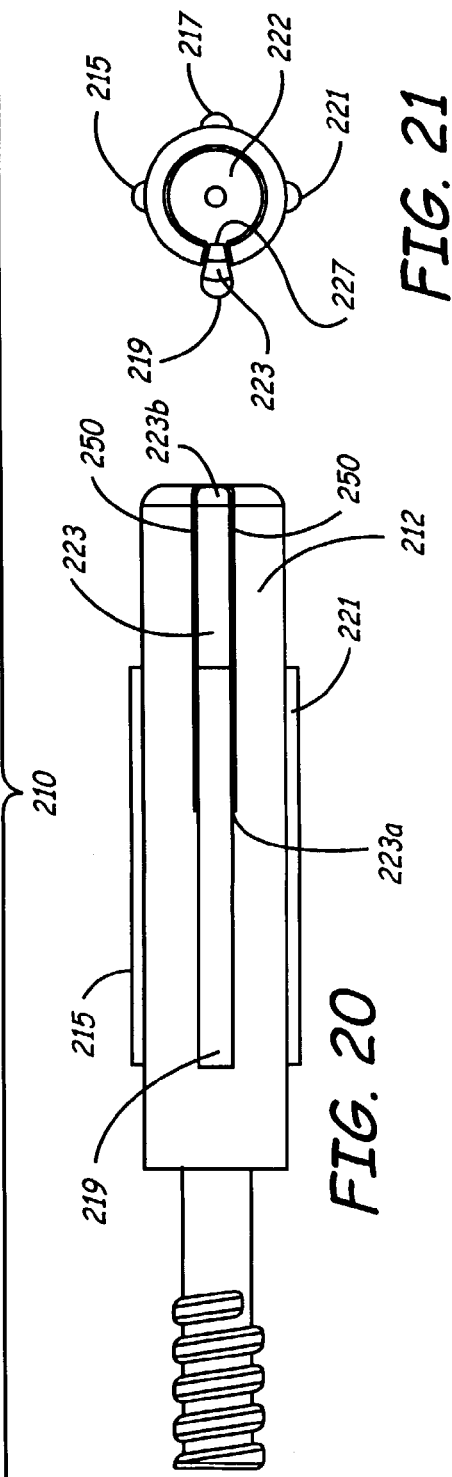

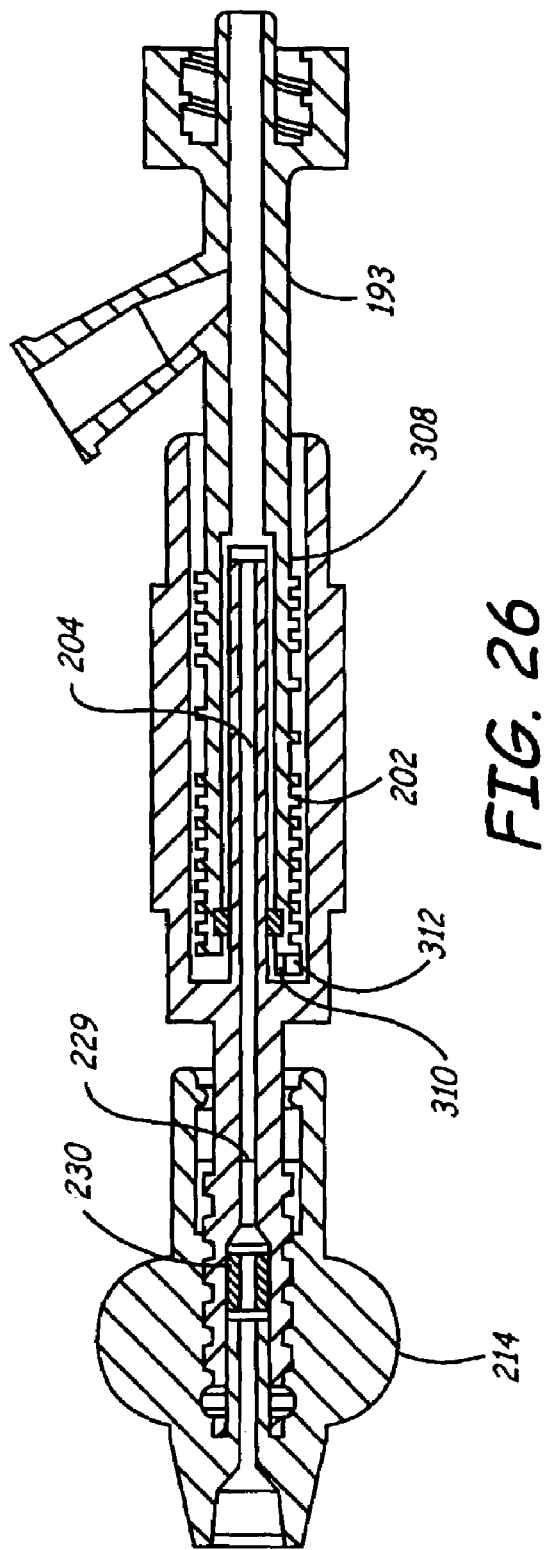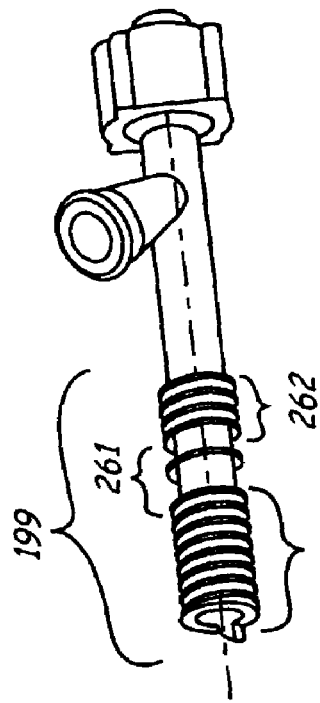

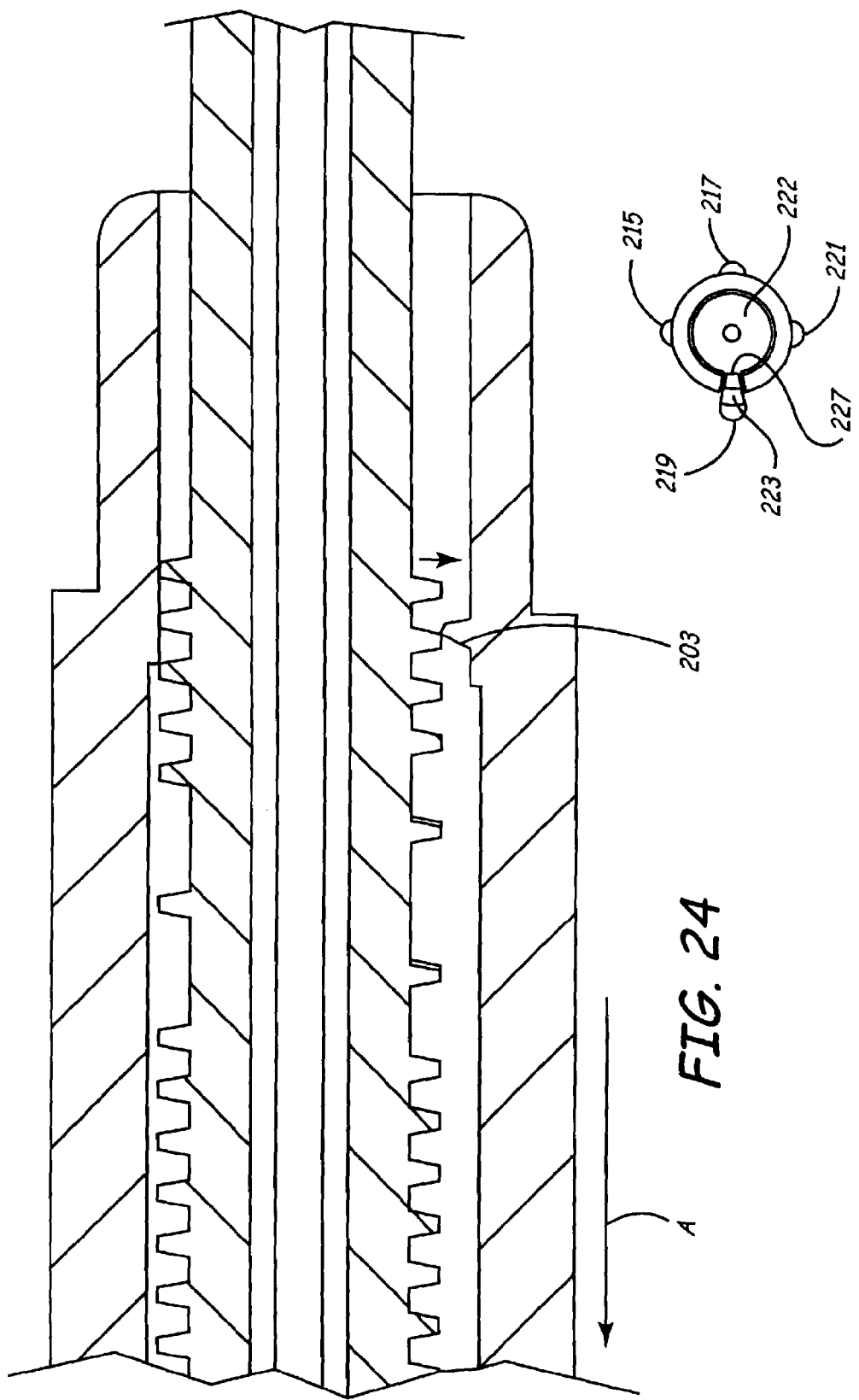

ARRANGEMENT FOR IMPLANTING A MINIATURIZED CARDIAC LEAD HAVING A FIXATION HELIX

FIELD OF THE INVENTION

The present invention relates to implantation of cardiac leads for applying electrical stimulation to and/or sensing electrical activity of the heart through one or more electrodes positioned at an implantation site within a heart chamber or cardiac vessel adjacent a heart chamber or into the myocardium from the epicardium and more particularly to an arrangement for introducing such a cardiac lead having low torqueability and pushability through a tortuous pathway and attaching the fixation helix of the cardiac lead at the implantation site.

BACKGROUND OF THE INVENTION

Implantable permanent and temporary medical electrical stimulation and/or sensing leads are well known in the fields of cardiac stimulation and monitoring, including cardiac pacing and cardioversion/defibrillation, and in other fields of electrical stimulation or monitoring of electrical signals or other physiologic parameters. In the field of cardiac stimulation and monitoring, the electrodes of epicardial or endocardial cardiac leads are affixed to the myocardium of the heart wall through either the epicardium or the endocardium, respectively, or bear against the epicardium or endocardium, respectively, or are lodged in a coronary vessel.

The lead body of a permanent or temporary cardiac lead typically includes one or more insulated conductive wires surrounded by an insulating outer sheath. Each conductive wire couples a proximal lead connector element with a distal stimulation and/or sensing electrode. Temporary and permanent cardiac leads having a single stimulation and/or sensing electrode at the lead distal end, a single conductor, and a single connector element are referred to as unipolar cardiac leads. Temporary and permanent cardiac leads having two or more stimulation and/or sensing electrodes at the lead distal end, two or more respective conductors, and two or more respective connector elements are referred to as bipolar lead or multi-polar leads, respectively.

Epicardial or myocardial permanent and temporary cardiac leads, or simply epicardial leads, are implanted by exposure of the epicardium of the heart typically through a limited thoracotomy or a more extensive surgical exposure made to perform other corrective procedures. Endocardial permanent and temporary cardiac leads, or simply endocardial leads, are implanted through a transvenous route to locate one or more sensing and/or stimulation electrode along or at the distal end of the lead in a desired implantation site in a chamber of the heart or a blood vessel of the heart. It is necessary to accurately position the electrode surface against the endocardium or within the myocardium or coronary vessel at the implantation site.

Temporary epicardial or endocardial cardiac leads are designed to extend through the patient's skin to an external monitor or pacing pulse generator to provide temporary pacing and to be removed from the patient's body when temporary pacing is halted. Permanent epicardial and endocardial cardiac leads are designed to be coupled to a pacemaker or defibrillator implantable pulse generator (IPG) or an implanted monitor and to be chronically implanted in the patient's body. The proximal end of such permanent cardiac leads typically is formed with one or more lead connector element that connects to a terminal of the IPG or monitor.

The complexity of the leads, the number of leads implanted in a common path, and the advancement of coronary sinus leads deep in a coronary vein have led to efforts to at least not increase and optimally to decrease the overall diameter of the cardiac lead body without sacrificing reliability and usability. More recently, it has been proposed to diminish the lead body further by eliminating the lumen for receiving the stiffening stylet and by reducing the gauge and coil diameter of the coiled wire conductor or replacing it with highly conductive stranded filament wires or cables. In bipolar or multi-polar leads, each such cable extends through a separate lumen of the lead body to maintain electrical isolation.

Over the last 30 years, it has become possible to reduce endocardial lead body diameters from 10 to 12 French (3.3 to 4.0 mm) down to 2 French (0.66 mm) presently through a variety of improvements in conductor and insulator materials and manufacturing techniques. The lead bodies of such small diameter, 2 French, endocardial leads must possess little if any column strength that could cause the lead distal end fixation mechanism and electrode to perforate through the myocardium during implantation and if the lead body were to become axially force-loaded during chronic implantation. As a result, the small diameter lead bodies lack "pushability", that is the ability to advance the lead distal end axially when the lead proximal end is pushed axially, particularly when the lead body extends through the tortuous transvenous pathway.

Such small diameter endocardial leads typically then require distal fixation to maintain the electrode(s) at the desired implantation site. Active fixation helices that extend axially in alignment with the lead body to a sharpened distal tip and that have a helix diameter substantially equal to the lead body diameter are preferred because the fixation mechanism does not necessarily increase the overall diameter of the endocardial lead and is relatively robust, once the helix is screwed into the myocardium. Typically, but not necessarily, the fixation helix is electrically connected to a lead conductor and functions as a pace/sense electrode. In some cases, the lead body encloses one or more helical coiled or stranded wire conductor and lacks a lumen.

The lead bodies of such small diameter endocardial screw-in leads are so supple and flexible that it is difficult to rotate the lead distal end by application of rotary torque to the lead proximal end unless the lead body remains relatively straight and not confined by contact with vessel walls. This diminished "torqueability" prevents the rotation of the fixation helix at the lead distal end or renders the rotation unreliable once the lead body is advanced through a tortuous pathway and confined by contact against the vessel walls. To the degree that rotation torque can be transmitted from the lead proximal end to the lead distal end, the active fixation helix at the lead distal end can be over-rotated and screwed through the myocardium or under-rotated and not screwed into the myocardium sufficiently. Thus, it has been found necessary to use implantation instruments or tools that compensate for the lack of pushability and torqueability of the lead body.

A first technique of implantation of such miniaturized, highly flexible, endocardial screw-in leads involve the use of a guidewire that is first advanced through the tortuous transvenous pathway. The endocardial lead is then advanced through the pathway alongside or over the guidewire as disclosed in U.S. Pat. Nos. 5,003,990, 5,304,218, 5,902,331, 6,132,456, and 6,185,464, for example. Some of these techniques require that the lead body be configured to provide an over-the-wire connection and possess sufficient column strength to be advanced over the guidewire. Other techniques employ elongated pusher tools that have sufficient column strength applied against the lead body distal end and extending alongside the lead body and the over the guidewire. These techniques are relatively complex to execute. Moreover, the rotation of the active fixation helix at the lead distal end through rotation of the assembly can still be problematic.

In commonly assigned U.S. Pat. No. 5,246,014, the introducer distal end and the lead distal end are configured to interlock or engage one another. The catheter, introducer and sheath lead body are advanced together through the transvenous, tortuous pathway to locate the fixation helix near the implantation site in the right atrium, right ventricle, coronary sinus, or cardiac vein. The fixation helix is pushed out of the catheter lumen distal end and the introducer catheter is rotated to screw the fixation helix into the myocardium by pushing and rotating the introducer proximal end extending proximally out of the catheter lumen outside the patient's body. In this approach, the inner introducer extends, in use, all the way to the catheter distal end. Thus, the catheter distal segment is stiffened and may be difficult to advance through the tortuous pathway. Certain embodiments of the interlocking mechanism also increase the diameter of the lead distal end.

A further technique of implantation of such miniaturized endocardial screw-in leads disclosed in commonly assigned U.S. Pat. No. 5,897,584 employs a flexible guide catheter having a catheter body that has sufficient pushability and resistance to kinking that it can be advanced through the transvenous pathway. The lead body is inserted into a catheter lumen during advancement of the catheter distal end and fixation helix to the implantation site. Then, it is necessary to rotate the fixation helix from the proximal end of the assembly to screw it into the myocardium at the implantation site. The distal advancement and rotation of the fixation helix is facilitated by a torque transfer device that is temporarily fitted over a proximal segment of the lead body extending proximally outside of the guide catheter hub and at a distance therefrom corresponding to or a fraction of the distance that the fixation helix is to be advanced distally to rotate it into the myocardium.

The torque transfer device frictionally engages the lead body segment and can be manipulated with one hand to distally advance the fixation helix from the guide catheter lumen and screw it into the myocardium at the implantation site. The torque transfer device is slipped sideways over and removed from the proximal lead body segment through an elongated slot and installation/removal and retention characteristics depend on the relative width of the slot and diameter of the lead body.

This technique requires selection of catheter body materials and characteristics that ensures that the catheter lumen is constant in diameter and resists making abrupt changes in direction as the catheter is advanced through the twists and turns of the tortuous pathway. The lead body diameter and materials must be selected to minimize binding of the lead body against the catheter sidewall in the twists and turns. Generally speaking, it becomes easier to advance the lead body through the catheter lumen as the catheter lumen diameter is increased. But, increasing the catheter body lumen renders advancing the guide catheter through the twists and turns and into small diameter coronary vessels more difficult.

As noted in the above-referenced '584 patent, the guide catheter typically is supplied with a hemostasis valve attached to the catheter hub and a side port that permits introduction of saline and anticoagulants to flush and lubricate the catheter lumen. But, tightening of the hemostasis valve to eliminate leakage alongside the lead body can negatively influence the pushability and torqueability of the lead body by manipulation of the torque transfer device.

In another approach, the lead body is enclosed within the lumen of a further sheath or introducer, and the lead and introducer are disposed within the lumen of the guide catheter. The fixation helix is located within the catheter lumen during advancement of the lead distal end fixation helix through the transvenous pathway and heart chamber or coronary vessel to dispose the fixation helix near the implantation site.

In further commonly assigned U.S. Pat. No. 6,408,214, the inner introducer, referred to as an inner sheath, and the outer catheter, referred to as an outer sheath each have preformed curves formed in distal sheath segments so that multiple curves can be induced as the inner and outer sheaths are axially adjusted relative to one another. The materials and dimensions of the inner and outer sheaths are selected to provide pushability and torqueablity of the assembly with the small diameter lead body disposed in the inner sheath lumen. The inner sheath is longer than the outer sheath, so that it can be selectively moved out of the outer sheath lumen to advance its distal tip to the implantation site. Again, the fixation helix is pushed out of the catheter lumen distal end and then rotated to screw the fixation helix into the myocardium by pushing and rotating the introducer proximal end extending proximally out of the catheter lumen outside the patient's body.

These approaches disclosed in the above-referenced '214 and '584 patent can suffer from the frictional engagement and binding of the lead body against the inner sheath or introducer sidewall as the physician rotates the proximal lead body segment. If the inner sheath lumen is made relatively larger in diameter than the lead body diameter to avoid such binding, the lead body tends to wind up within the inner sheath lumen when it is rotated. Tactile feedback to the physician through the lead body of the rotation of the distal fixation helix as the proximal segment is rotated is lost due to binding or winding up within the sheath lumen. It is difficult for the physician to determine just how far the lead body distal segment has been advanced and how many rotations that the fixation helix has actually made.

Typically, it is only necessary to rotate the fixation helix the number of turns of the helix, e.g., two complete turns, to fully embed the helix into the myocardium. But, it may be necessary to rotate the proximal segment of the lead body through multiple turns, such as approximately four to nine turns, for example, depending on the lead length and the tortuosity of the pathway, to cause the applied torque to overcome windup of the lead body and rotate the distal fixation helix the requisite two turns. The physician cannot be certain that the distal fixation helix has rotated the requisite two turns or has over-rotated, possibly causing higher thresholds, and has perforated or is in danger of perforating through the myocardium.

Moreover, instruments, e.g., cardiac leads, guidewires, balloon catheters, etc advanced through guide catheter lumens typically are passed through a penetrable and resealable hemostasis valve incorporated into the guide catheter hub. The hemostasis valve bears against the instrument body to prevent leakage of fluids within the guide catheter lumen. Advancement of guidewires and balloon catheters and other instruments having column strength is not impeded by the contact with the hemostasis valve. However, it is difficult to pass cardiac leads of the types described above lacking appreciable column pushability and torqueability through such hemostasis valves.

Thus, a need remains for an introducer system for a small diameter screw-in lead lacking pushability and torqueability that enables advancement of the fixation helix through tortuous pathways into a wide variety of implantation sites in a heart chamber or in a coronary vessel of the left heart chambers and reliable fixation at the selected implantation site. Such a system is needed that provides the physician with positive feedback of the number of turns that the lead body is rotated to rotate the fixation helix the requisite number of turns into the myocardium. The above-described problem with the passage of a cardiac lead through a guide catheter hemostasis valve needs to be eliminated.

Preferably, such a lead introducer system would also be of use in implanting small diameter epicardial screw-in leads through minimally invasive approaches through the thorax to the epicardium of the heart, particularly implantation sites of the left heart chambers.

SUMMARY OF THE INVENTION

The present invention provides an introducer system that can be employed to introduce and fix a distal fixation helix of a cardiac lead at a desired implantation site in a heart chamber or cardiac blood vessel or the epicardium of the heart that satisfies these needs. The introducer system is adapted to introduce a small diameter cardiac lead having a lead body enclosing a lead conductor(s) and extending between a proximal lead connector element(s) and a distal electrode(s) and fixation helix through a tortuous pathway to the heart, wherein the lead body has insufficient pushability and torqueability to be easily advanced by itself through the tortuous pathway, to locate and attach the fixation helix at a desired implantation site.

In an embodiment of the present invention, introducer system includes a torque transfer sheath, extending from a proximal end to a distal end, receiving the lead, an outer sheath, having a distal end, receiving the lead positioned within the torque transfer sheath, and a handle operable between a first handle position enabling advancement and retraction of the lead through the handle and a second handle position fixedly engaging a proximal end of the lead within the handle. The lead is advanced through the outer sheath to extend outward a predetermined distance from the distal end of the outer sheath and the fixation helix is rotated through the predetermined distance to be fixedly engaged at the implantation site in response to simultaneous rotation and advancement of the lead and the torque transfer sheath through rotation and advancement of the handle in the second handle position.

In another embodiment of the present invention, the introducer system includes a torque transfer sheath, extending from a proximal end to a distal end, receiving the lead, an outer sheath, having a distal end, receiving the lead positioned within the torque transfer sheath, and a hub body, extending from a proximally extending portion having a threaded portion positioned thereon to a connecting portion, the outer sheath and the hub body being fixedly engaged through threaded interaction of mating threads formed between the outer sheath and the connecting portion of the hub body. A handle shaft having an axial bore extends through the length of the handle shaft from a proximal portion to a distal portion formed to receive the proximally extending portion of the hub body. A first engaging member is positioned within the proximal portion of the axial bore, and a cap is advanced distally towards the handle shaft to engage the first engaging member against the lead to position the cap in a first cap position fixedly engaging the lead within the handle shaft and is retracted proximally from the handle shaft to disengage the second engaging member from the lead to position the cap in a second cap position enabling advancement of the lead through the handle shaft. Finally, a second engaging member is positioned within the distal portion of the axial bore and advances through grooves formed by the threaded portion of the hub body to distally advance the handle shaft when the cap is in the first cap position as the handle shaft is rotated about the proximally extending portion. The proximal end of the torque transfer sheath is fixedly positioned within the proximal portion of the handle shaft and the rotation of the handle shaft about the proximally extending portion of the hub body when the cap is in the first cap position transmits torque through the torque transfer sheath to the lead to screw the fixation helix extending from the distal end of the outer sheath body into the implantation site.

In yet another embodiment of the present invention, a method for positioning and fixedly engaging a distal fixation helix of a lead at an implantation site within a patient's body includes inserting a lead through a handle and a torque transfer sheath while the handle is in a first handle position enabling advancement and retraction of the lead through the handle and extending a distal fixation helix of the lead outward a predetermined distance from an outer sheath distal end; fixedly engaging the lead body within the handle; retracting the lead and the torque transfer sheath within the outer sheath to advance the fixation helix within the outer sheath; positioning the outer sheath at the implantation site; and rotating the handle to rotate and advance the lead and the torque transfer sheath simultaneously through the outer sheath to extend the fixation helix outward a predetermined distance from the end of the outer sheath and to rotate the fixation helix through the predetermined distance to be fixedly engaged at the implantation site.

In still another embodiment of the present invention, an introducer system for positioning and fixedly engaging a distal fixation helix of a lead at an implantation site including a cap includes means for selectively fixedly positioning the lead within a first portion of a handle; means for controlling rotation of a second portion of the handle simultaneously with the first portion to advance the fixation helix to extend outward a predetermined distance from a distal end of an outer sheath and to rotate the fixation helix a predetermined number of turns; and means for transmitting torque corresponding to the rotation of the first portion and the second portion of the handle by the controlling means to a distal portion of the lead to rotate the fixation helix the predetermined number of turns.

This summary of the invention and the advantages and features thereof have been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

Other advantages and features of the present invention will be readily appreciated as the same becomes better understood by reference to the following detailed description when considered in connection with the accompanying drawings, in which like reference numerals designate like parts throughout the figures thereof and wherein:

FIG. 5 is a plan view of an elongated guide catheter or outer sheath of the introducer system adapted to be advanced through the tortuous pathway from outside the patient's body to the implantation sites illustrated in FIGS. 1 and 2, for example;

FIG. 6 is a plan view of a torque transfer tool of the introducer system through which the cardiac lead of FIG. 3 extends, the torque transfer tool comprising an elongated torque transfer sheath body adapted to be disposed in a proximal segment of the outer sheath lumen of the outer sheath of FIG. 5, and a proximal torque transfer handle shown in the released position, whereby the cardiac lead can be moved proximally or distally within the tool lumen;

FIG. 7 is a cross-section view of the torque transfer tool of FIG. 6 taken along line 7—7 showing the release of the lead body in the tool lumen;

FIG. 8 is a plan view of the torque transfer tool of FIG. 6 shown in the locked position, whereby the cardiac lead is gripped and prevented from being moved proximally or distally within the tool lumen and enabling torque applied to the tool handle to be imparted to the cardiac lead body within the torque transfer sheath body lumen to rotate the distal fixation helix into the implantation site;

FIG. 9 is a cross-section view of the torque transfer tool of FIG. 8 taken along line 9—9 showing the gripping of a portion of the lead body in the tool lumen;

FIG. 15 is a plan view of the proximal portion of the combined introducer system, wherein the torque transfer tool and the outer sheath are depicted in the locked and distally extended configuration;

FIG. 16 is a cross-section view of the proximal portion of the combined torque transfer tool and outer sheath taken along line 16—16 of FIG. 15;

FIG. 17 is a plan view of the proximal portion of the combined introducer system, wherein the torque transfer tool and the outer sheath are depicted in the unlocked and proximally retracted position;

FIG. 18 is a cross-section view of the proximal portion of the combined torque transfer tool and outer sheath taken along line 18—18 of FIG. 17;

FIG. 19 is an exploded, cross-section, expanded view of the components of the torque transfer tool of the combined introducer system comprising a tubular distal handle shaft, an elastic gripping ring and a proximal handle cap;

FIG. 20 is an expanded plan view of the tubular distal handle shaft;

FIG. 21 is an expanded end view of the tubular distal handle shaft;

FIG. 22 is a schematic diagram of a torque tool hub body according to the present invention;

FIG. 24 is a cross-sectional view of a hub body and a tooth of a handle shaft of a torque transfer tool, according to the present invention, with the tooth of the handle shaft in a non-engaged position;

FIG. 25 is an end view of a tubular handle shaft of the present invention;

FIG. 26 is a cross-sectional view of a torque transfer tool according to an alternate embodiment of the present invention.

Figure 1:
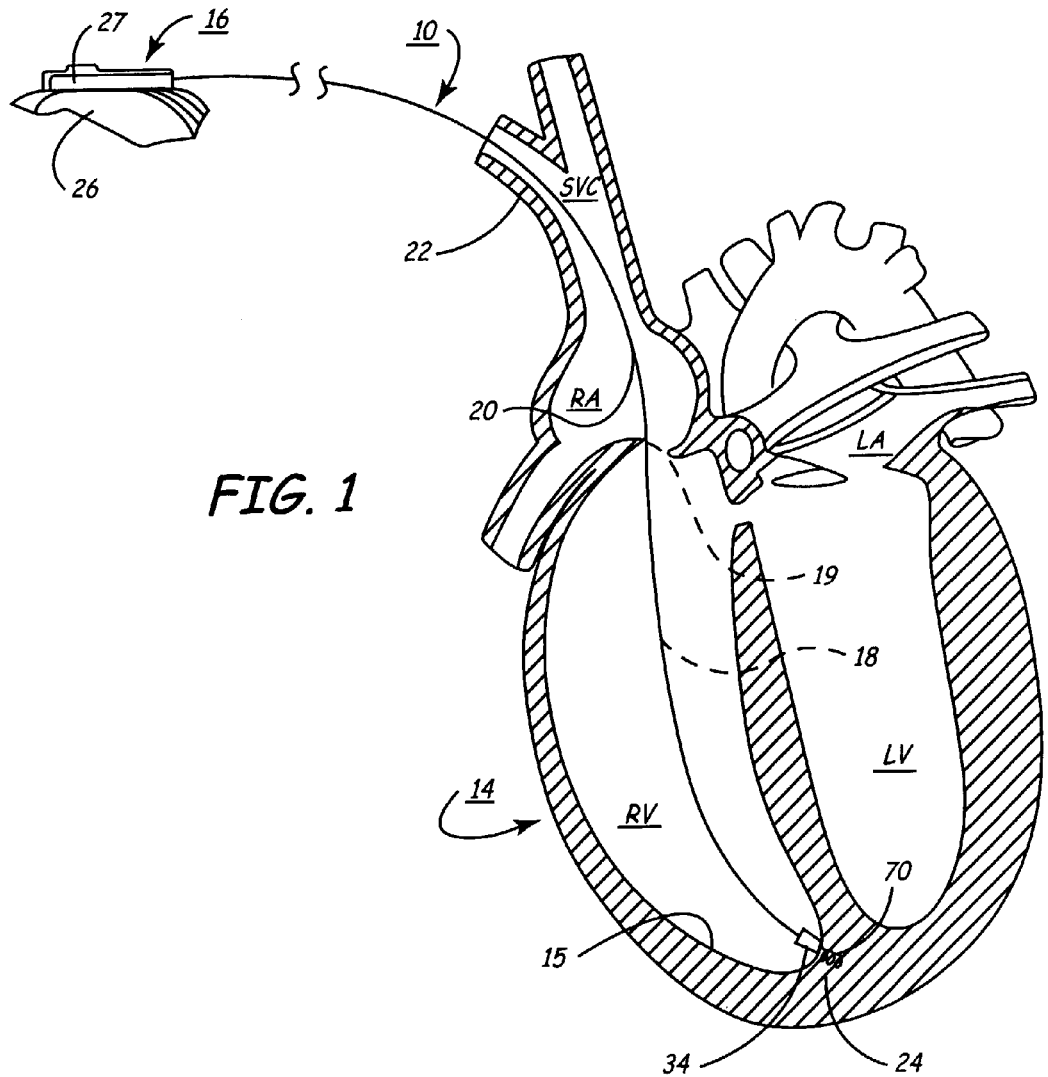
FIG. 1 is a schematic representation of a right heart cardiac lead bearing at least one cardiac electrode introduced into one of several illustrated implantation sites of the right heart chambers and coupled at the proximal lead connector end to an implantable medical device.

It is understood that the drawing figures are not necessarily to scale.

DETAILED DESCRIPTION OF THE INVENTION

In the following detailed description, references are made to illustrative embodiments for carrying out the invention. It is understood that other embodiments may be utilized without departing from the scope of the invention. The invention and its preferred embodiment may be implemented in unipolar, bipolar or multi-polar, endocardial, cardiac pacing or monitoring leads having one or more pace/sense electrode(s) or sense electrode(s), respectively, at or adjacent the distal lead end. Similarly, the invention and its preferred embodiment may be implemented in cardiac defibrillation/cardioversion leads including at least one cardioversion/defibrillation electrode and optionally including one or more pace/sense electrode(s) at or adjacent the distal lead end. Moreover, other sensors for sensing a physiologic parameter may be incorporated into the lead body. Each such pace/sense electrode, sense electrode, cardioversion/defibrillation electrode and sensor is coupled with an insulated electrical conductor extending proximally through the lead body to a lead proximal end connector assembly. The proximal connector end assembly is adapted to be coupled to the connector assembly of an external medical device, including an external pacemaker or monitor, or an implantable medical device, including an IPG for pacing, cardioversion/defibrillation or both or an implantable monitor. Therefore, it will be understood that the arrangement for introduction of a cardiac lead of the present invention can be employed to introduce permanently implantable and temporary cardiac leads of these types.

The arrangement of the present invention is particularly useful in introducing such small diameter cardiac leads that are devoid of a stylet lumen and are so flexible and possess such low column'strength, pushability and torqueability that the lead distal end cannot be advanced transvenously and positioned at the desired implantation site without assistance. Moreover, one particular use of the arrangement of the present invention is to introduce such cardiac leads that are formed using stranded wire conductor(s) within a lead body diameter of about 0.010–0.035 (0.254–0.889 mm) inches of the type described in the above-incorporated, commonly assigned, '014 patent. The lead body outer diameter is minimized by use of such conductors and by eliminating the lumen for receiving a stiffening stylet. However, the arrangement of the present invention can also be employed to introduce cardiac leads that employ coiled wire conductors with or without a lumen for receiving a stiffening stylet. In the latter case, the stiffening stylet need not be used to achieve the introduction.

Figure 2:
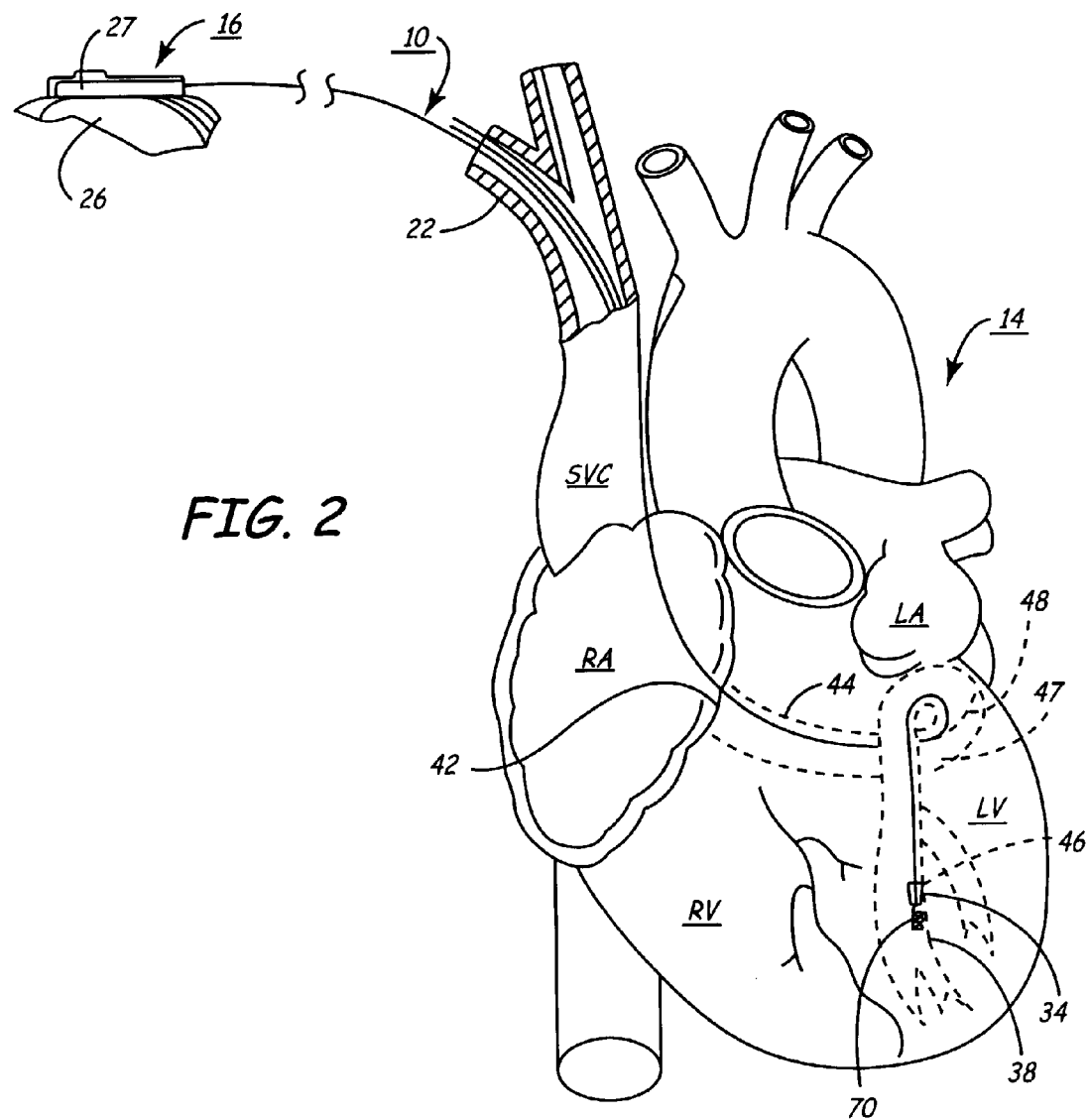
FIG. 2 is a schematic representation of a coronary sinus cardiac lead bearing at least one cardiac electrode introduced into one possible implantation sites within the cardiac vein adjacent to left heart chambers and coupled at the proximal lead connector end to an implantable medical device.

FIGS. 1 and 2 are schematic representations of a cardiac lead 10 introduced into implantation sites of the right heart or the coronary vessels branching from the coronary sinus (CS). The cardiac leads 10 are introduced to the implantation sites in the cardiac blood vessels or chambers of the heart 14 through a tortuous pathway from a skin incision and venotomy made through the venous system, e.g., the right or left cephalic vein, other subclavian branches or the external or internal jugular vein in a manner well known in the art.

The proximal lead connector elements are schematically illustrated coupled in each instance to an implantable medical device (IMD) 16 of any of the above noted types. In FIGS. 1 and 2, heart 14 includes the upper heart chambers, the right atrium (RA) and left atrium (LA), and the lower heart chambers, the right ventricle (RV), and the left ventricle (LV). The coronary sinus (CS) is also depicted schematically in FIG. 2 extending from the opening 42 in the RA and extending laterally around the atria as the cardiac vein 44 and into the anterior interventricular vein 46 descending inferiorly along the LV.

The IMD 16 (depicted partially) is implanted subcutaneously, i.e., below the skin, after it is connected to the lead connector element(s) and includes electronic components and a power supply enclosed with a housing 26 and a connector block 27. Connector block 27 has one or more bore for receiving the proximal lead connector element(s) of the cardiac lead 10 introduced into a right heart chamber or the CS. These figures illustrate some of the possible implantation sites and routes of introduction of cardiac electrodes on cardiac lead 10 to the implantation sites in accordance with the method and apparatus of the present invention. It will be understood that the illustrated right heart and CS cardiac leads 10 may be implanted at the implantation sites in the heart 14 and coupled to the connector block 27 of a suitable IMD 16. The illustrated cardiac lead 10 can have a unipolar, bipolar or multi-polar configuration and can be fabricated with pace/sense and/or cardioversion/defibrillation electrodes. Alternatively, the cardiac lead 10 can simply bear EGM sensing electrodes and/or physiologic sensors. The present invention is related to introduction arrangement and methods for introducing a cardiac electrode and/or physiologic sensor to one of the illustrated sites and other suitable implantation sites.

For simplicity, a unipolar right heart cardiac lead 10 is shown in FIG. 1 extending through the superior vena cava (SVC) 22 inferiorly through the RA and RV and lodging a distal electrode 34 and fixation helix 70 into the implantation site 24 in the RV apex of the heart 14. The cardiac lead 10 is formed having an elongated lead body extending between a connector element at a lead body proximal end (depicted inserted within a bore of the IMD connector block 27) and the distal fixation helix 70 extending distally from the lead body distal end. An electrode 34 is also supported extending to or adjacent to the lead body distal end, and a lead conductor extends within the lead body between the connector element and the electrode 34. The distal cardiac electrode 34 can be combined with the distal fixation helix 70 or be located along the lead body proximal to the fixation helix 70. Thus, the distal cardiac electrode 34 can be at or adjacent to (i.e., contiguous to) the lead body distal end.

In FIG. 1, the distal fixation helix 70 is adapted to be screwed into the myocardium and provide active fixation therewith through use of the introduction arrangement and method of the present invention as described hereafter. For example, FIG. 1 illustrates that the fixation helix 70 can be affixed at an implantation site 24 deep in the RV apex or in other implantation sites 19 and 18 in the septum between the RV and LV chambers when the lead 10 is implanted in the RV. The fixation helix 70 can alternatively be implanted in the RA with the fixation helix 70 screwed into an implantation site 20 of relatively thicker areas of the RA, e.g., the exterior right atrial wall or the right atrial appendage. It will also be understood that the fixation helix 70 can also simply attach the distal end of the cardiac lead 10 to the depicted implantation sites 18, 19 and 24 of the RV and the implantation site 20 of the RA (or other selected implantation sites of the RA and RV) and a separate cardiac electrode 34 can be provided on the lead body.

FIG. 2 illustrates the introduction of the cardiac lead 10 through the SVC and RA chamber and the ostium of the CS to extend alongside the LA chamber and the LV. The distal electrode(s) 34 can be located as depicted deep within the anterior interventricular vein 46 at LV implantation site 38 adjacent to the LV for LV stimulation and/or sensing applications, or the distal electrode(s) 34 can be located in the cardiac vein 47 at an implantation site 48 adjacent to the LA to provide LA stimulation and/or sensing applications, for example. The distal fixation helix 70 is adapted to be screwed into the coronary vessel wall at the implantation site 38, 48 or other site within the coronary vessels and provide active fixation therewith through use of the introduction arrangement and method of the present invention as described hereafter.

Figure 3:
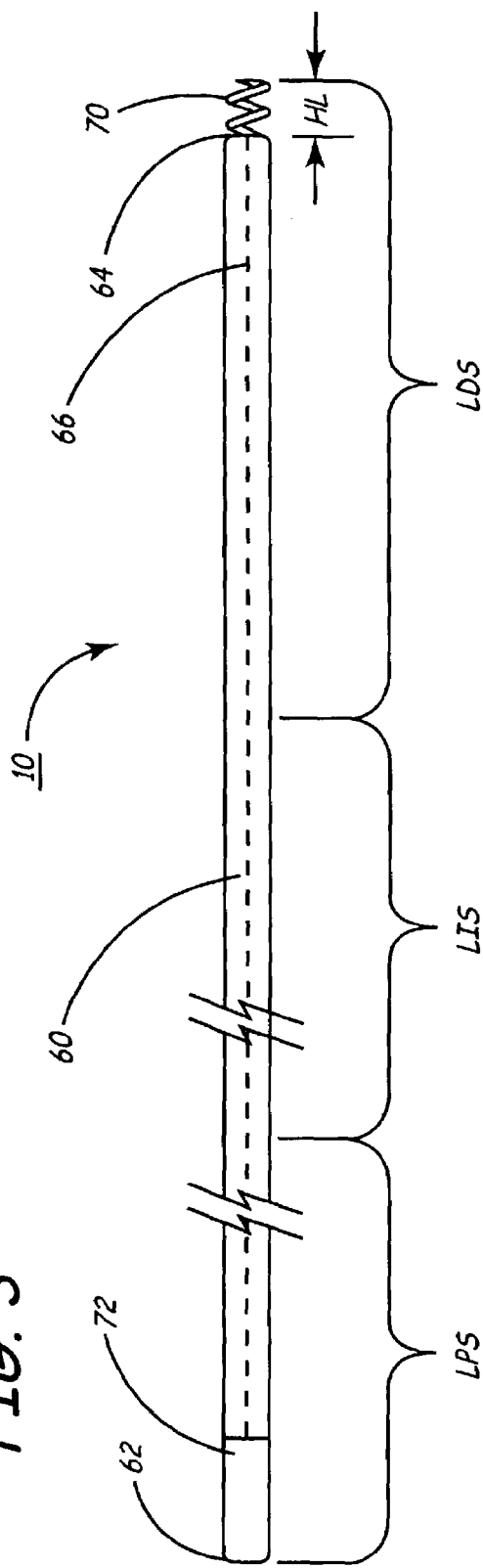
FIG. 3 is a plan view of an exemplary cardiac lead usable as a right heart cardiac lead or coronary sinus lead implanted at any of the implantation sites illustrated, for example, in FIGS. 1 and 2 employing the introducer systems of the present invention.
Figure 4:
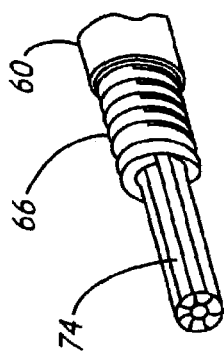
FIG. 4 is an expanded detail view of the construction of the lead body of the cardiac lead of FIG. 3.

An exemplary unipolar cardiac lead 10 that can be implanted in the sites depicted in FIGS. 1 and 2, for example, is depicted in FIGS. 3 and 4. As illustrated in FIGS. 3 and 4, the cardiac lead 10 includes an elongated lead body 60 extending between a connector element 72 at a lead body proximal end 62 and a fixation helix 70 at the lead body distal end 64. The fixation helix 70 includes the electrode 34 in this illustrated example, and a lead conductor 66 extends within the lead body 60 between the connector element 72 and the distal fixation helix 70. The cardiac lead 10 is depicted in FIG. 3 having a lead proximal segment LPS, a lead intermediate segment LIS, and a lead distal segment LDS including the distal fixation helix 70 having a helix length HL.

The introducer methods and systems of the present invention enable the implantation of a small diameter lead body 60 in the range of 1 French (0.33 mm) to 3 French (1.00 mm), but it will be understood that the introducer systems can be sized to facilitate implantation of larger diameter lead bodies exceeding 3 French in diameter. The lead body 60 can be formed in a variety of ways, and one example is depicted in FIG. 4. The illustrated exemplary lead body 60 includes a single-filar or multi-filar helical conductor 66 that is wound about a flexible conductive cable or a non-conductive tensile fiber 74 that is mechanically attached to the proximal and distal lead body ends 62 and 64. The cable or fiber 74 provides tensile strength to the lead body 60. However, the lead body 60 is highly flexible and may not possess column strength sufficient to push the fixation helix through the tortuous pathways illustrated in FIGS. 1 and 2 or torque-ability sufficient to rotate the fixation helix 70 into the myocardium or vessel wall by rotating the lead proximal segment LPS from the incision outside the patient's body.

It will be understood that the introducer systems and methods of use disclosed herein can be employed to introduce and secure any form of distal fixation helix either extending distally like distal fixation helix 70 or laterally from the lead body in the manner of those distal fixation helices disclosed in U.S. Pat. Nos. 3,835,864 and 4,233,992, for example.

An exemplary elongated guide catheter or outer sheath 80 adapted to be advanced through the tortuous pathway from outside the patient's body to the implantation sites illustrated in FIGS. 1 and 2, for example, is illustrated in FIG. 5. In a preferred embodiment, the outer sheath 80 of the introducer system includes an outer sheath body 82 extending from a proximal outer sheath hub body 90 to an outer sheath distal end 88. The outer sheath body 82 can take any of the known forms having a length of about 25 cm to 120 cm depending upon the selected pathway from the skin incision through the body to the implantation site and an outer sheath body lumen 84 extending the length of the outer sheath body 82 to a distal lumen end opening 89 at the outer sheath body distal end 88. The outer sheath 80 can take the form of a guide catheter of the types described in the above-referenced commonly assigned '584 patent and others known in the art.

The outer sheath hub body 90 includes a hub lumen 92 extending through the length of the hub body 90, with a branch of the hub lumen 92 extending through a side port 94. The side port 94 is coupled with an aspiration source or an infusion source, or is capped or includes a valve that can be opened and closed to selectively provide aspiration or fluids from or infusion of fluids into the hub lumen 92 and the outer sheath body lumen 84 in a manner well known in the art. A penetrable septum 96 is entrapped by a cap 98 to extend across the hub lumen 92 at the proximal end of the hub body 90 to function as a conventional Luer type hemostasis valve inhibiting loss of blood or fluids alongside any instrument extended through it in a manner well known in the art. The hub lumen 92 and outer sheath body lumen 84 are axially aligned and constitute the outer sheath lumen 84.

Figure 10:
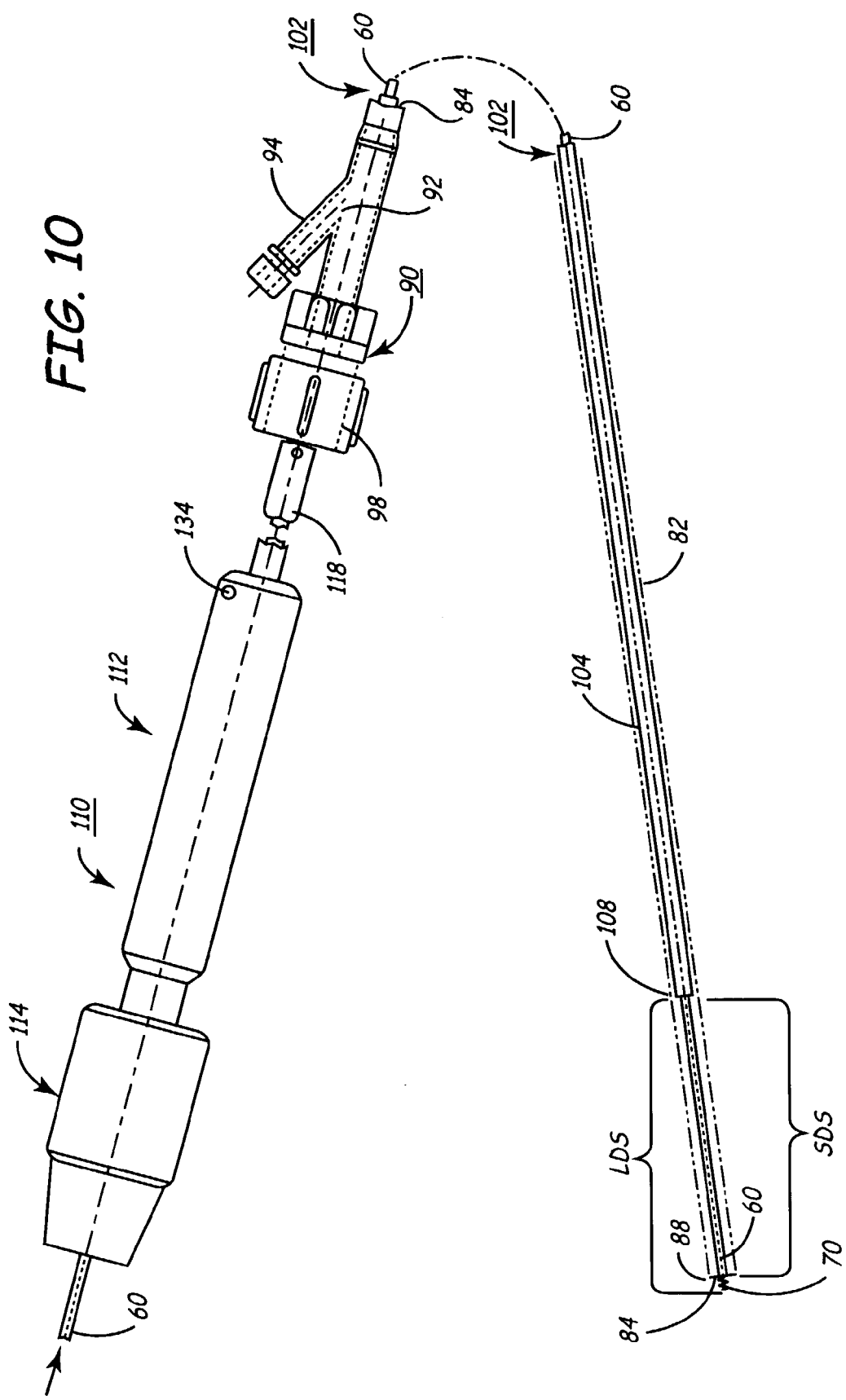
FIG. 10 is a plan view of the assembly of the sub-assembly of the torque transfer tool and cardiac lead of FIG. 6 with the outer sheath of FIG. 5 wherein the torque transfer sheath body is inserted fully into the outer sheath lumen and depicting the advancement of the cardiac lead body through the torque transfer sheath body lumen and the distal segment of the outer sheath lumen to expose the distal fixation helix prior to locking the torque transfer tool to grip the cardiac lead body.
Figure 11:
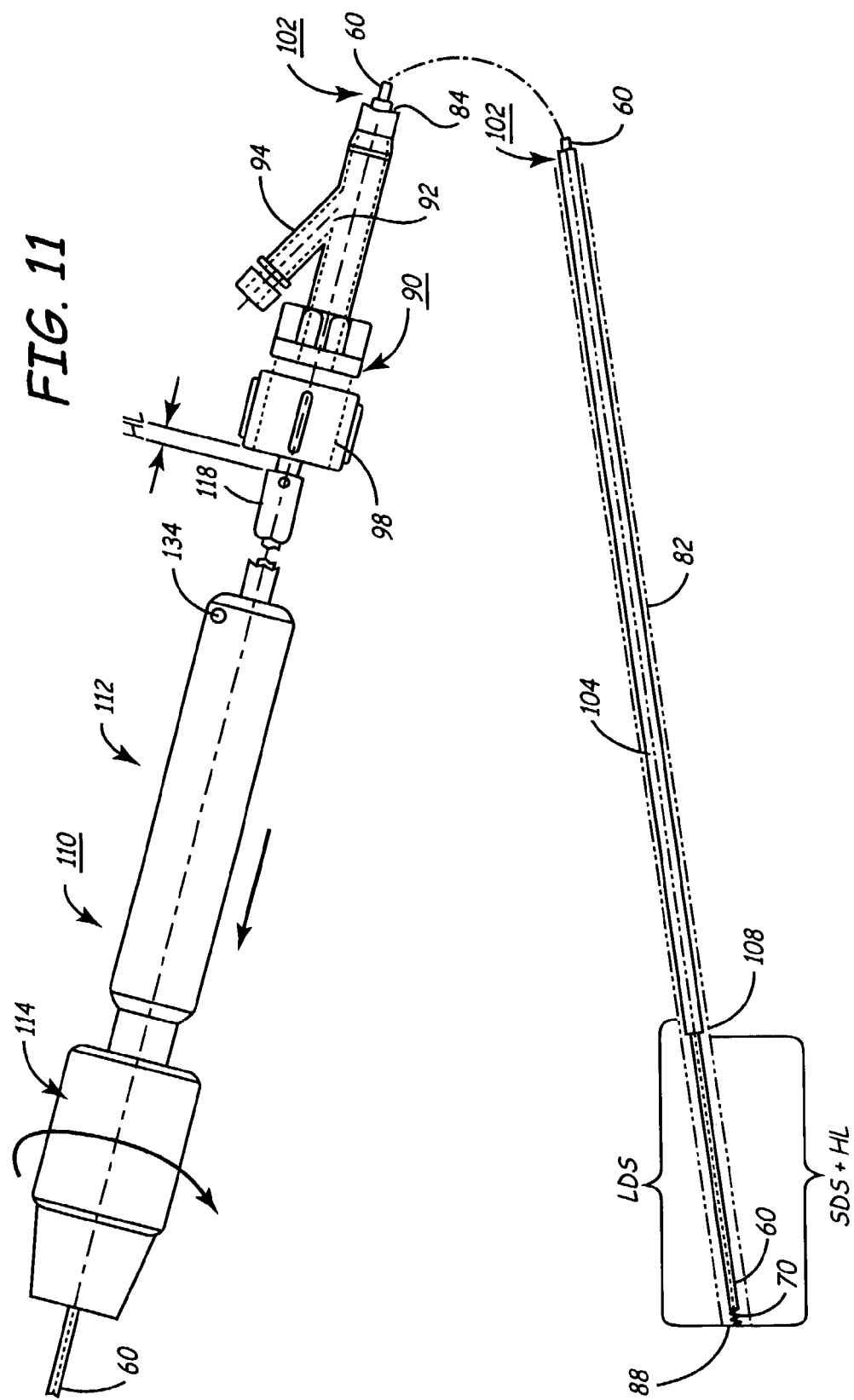
FIG. 11 is a further plan view of the assembly of the sub-assembly of the torque transfer tool of FIG. 6 with the outer sheath of FIG. 5 wherein the torque transfer tool is in the locked position to grip the cardiac lead body and the torque transfer sheath body is retracted proximally at least the length of the distal fixation helix to retract the distal fixation helix into the distal segment of the outer sheath lumen during advancement through the tortuous path to the implantation sites of FIGS. 1 and 2, for example.
Figure 12:
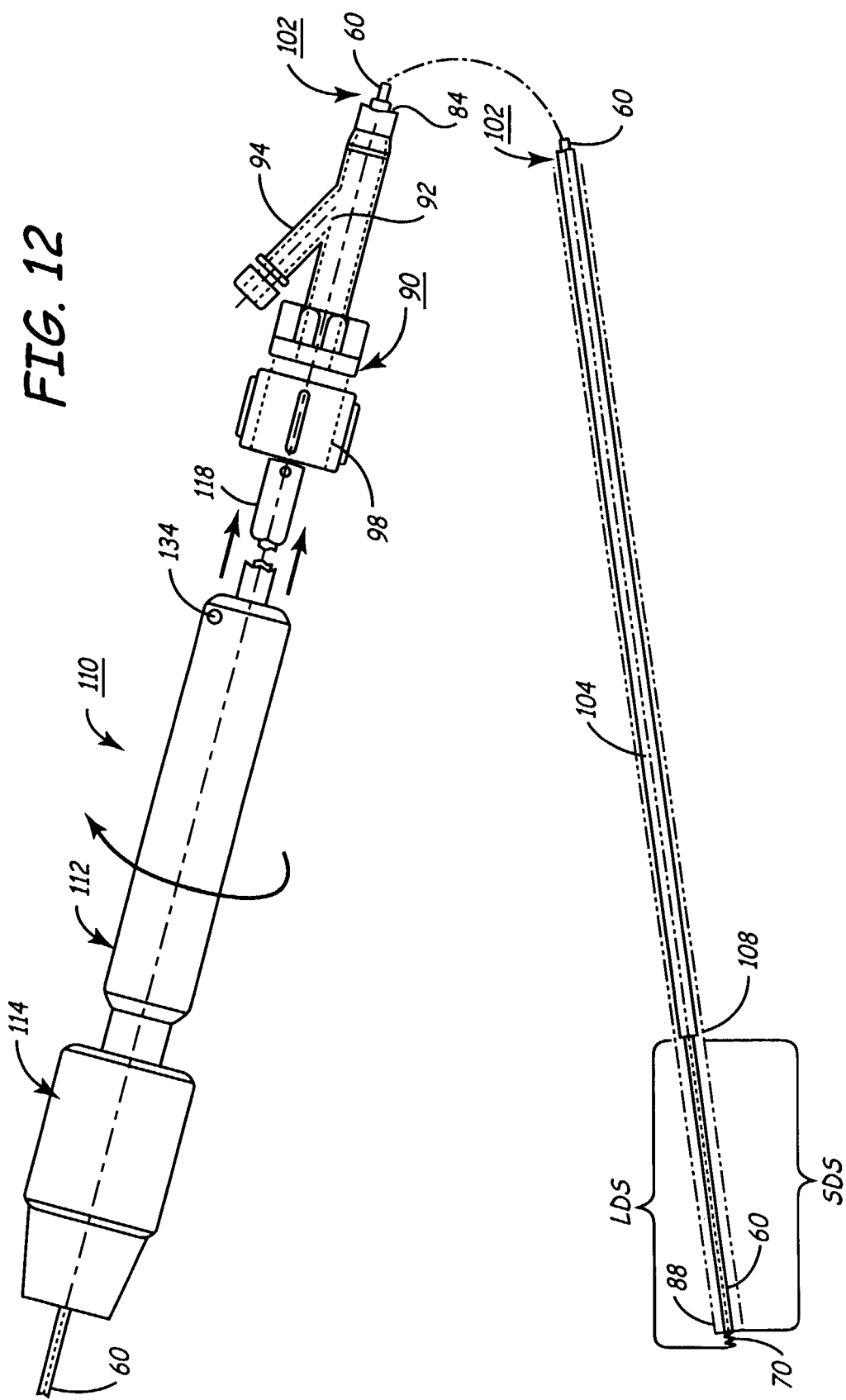
FIG. 12 is a still further plan view of the assembly of the sub-assembly of the torque transfer tool of FIG. 6 with the outer sheath of FIG. 5 wherein the torque transfer tool is in the locked position to grip the cardiac lead body and the torque transfer sheath body is advanced distally at least the length of the distal fixation helix to extend the distal fixation helix from the distal segment of the outer sheath lumen so that the distal fixation helix can be fixated into cardiac tissue at the implantation site through torque applied to the torque transfer tool handle.

The lead 10 of FIG. 3 is depicted in sub-assembly with a torque transfer tool 100 of the introducer system in FIGS. 6–9 and in assembly with the torque transfer tool 100 and the outer sheath 80 in FIGS. 10–12. As illustrated in FIGS. 6–12, the torque transfer tool 100 according to the present invention includes an elongated torque transfer sheath 102 and a torque transfer tool handle 110. The torque transfer sheath 102 is preferably formed of a torque transfer sheath body 104 that includes a length of thin walled tubing formed of a polymer, e.g., polyimide or PEEK, polyetherimide, etc., or other polymer possessing desired rigidity, kink-resistance, and flexibility and having a wall thickness that will emphasize size, flexibility, and torque performance, e.g., about 0.0025 inches (0.063 mm). The diameter of a torque transfer sheath body lumen 106 extending through the torque transfer sheath body 104 is selected to tightly encase the lead body 60 to support the lead body 60, providing a clearance between the lead body diameter and the surface of the torque transfer sheath body lumen 106 that will allow easy removal after lead fixation, e.g., about 0.002–0.010 inches (0.051–0.254 mm clearance for a 2.6 French or 0.286 mm diameter lead). The material chosen for the torque transfer sheath body 104 must possess a wall thickness, diameter, length and durometer that provides the ability to transmit torque through the torque transfer sheath body length ISL while restrained within the outer sheath body lumen 84 and possibly while in sliding contact with the inner surface of outer sheath body lumen 84.

Advantageously, the torque transfer sheath 102 isolates the lead body intermediate segment LIS from contact with the surface of outer sheath body lumen 84.

In the embodiment of the present invention illustrated in FIGS. 6–12, the torque transfer sheath 102 is adapted to be disposed in the outer sheath body lumen 84 extending through a sheath proximal segment SPS depicted in FIG. 5 when the elongated torque transfer sheath body 104 is fully advanced through septum 96, hub lumen 92, and into outer sheath body lumen 84. The clearance between the outer diameter of the torque transfer sheath body 104 and the surface of the outer sheath body lumen 84 is selected to allow rotation and axial movement of the torque transfer sheath body 104 within outer sheath body lumen 84, e.g., between 0.010 mm and 0.200 mm. A clearance of about 0.005 inches (0.012 mm) around the circumference of the torque transfer sheath body 104 was found to be satisfactory. A sheath distal segment SDS of the outer sheath body 82 distal to the distal end 108 of the fully inserted torque transfer sheath body 104, including the helix length HL, is also depicted in FIG. 5.

Therefore, the elongated torque transfer sheath 102 includes a torque transfer sheath body 104 that is shorter in length than the outer sheath body 82 and that extends from the torque transfer handle 110 to a torque transfer sheath body distal end 108. The torque transfer sheath body 104 can be advanced distally into and proximally out from the sheath proximal segment SPS through the septum 96. The torque transfer sheath length ISL corresponds to the length of the outer sheath proximal segment SPS when torque transfer sheath body 104 is fully inserted into the outer sheath body lumen 84. The lead body 60 can be axially advanced through the torque transfer sheath body lumen 106 and locked in place by clamping the lead body 60 and torque transfer handle 110 together as described further below.

The torque transfer handle 110 is preferably formed of a handle shaft 112 affixed to a proximal segment of the torque transfer sheath body 104 and a cap 114 adjustably affixed to the handle shaft 112. A tool lumen 116 extends through the handle shaft 112 and cap 114 in axial alignment with the torque transfer sheath body lumen 106 for insertion of the lead body 60 through the tool lumen 116 and the torque transfer sheath body lumen 106 as shown in FIGS. 6–12. The tool lumen 116 is adapted to be selectively narrowed by adjustment of the cap 114 with respect to the handle shaft 112 so that the tool handle 110 grips a portion of the lead body 60 to enable rotation of the torque transfer sheath 102 and the lead body 60 within the torque transfer sheath body lumen 106 by rotation of the torque transfer handle 110 without damage to the lead body 60. In the preferred embodiment, an elastic gripping ring 130 is selectively compressed about a portion of the lead body 60 to grip the lead body 60 by adjusting the cap 114 with respect to the handle shaft 112.

As illustrated in FIGS. 7 and 9, the handle shaft 112 is formed of an outer tubular shell 122 of rigid thermoplastic material, for example, that encloses a relatively flexible strain relief tube 118 disposed around a proximal segment of the torque transfer sheath body 104. Strain relief tube 118 is maintained in a bore of the tubular shell 122 by adhesive 132 and extends proximally therefrom. The tubular shell 122 also supports and encloses (at least in part) elastic gripping ring 130 that a most proximal segment 125 of the torque transfer sheath body 104 extends into and the tool lumen 116 extends through. The elastic gripping ring 130 can be formed of an elastic material, e.g., silicone rubber, that assumes the shape depicted in FIG. 7 when not compressed enabling free passage of the lead body 60 through the tool lumen 116 and the shape depicted in FIG. 9 when compressed about the lead body 60.

The cap 114 is formed of an outer rigid shell 124 that includes an end wall 117 forming a cup-shaped interior space 126 that extends distally over the proximal end of the tubular shell 122 and the elastic gripping ring 130 and an end opening forming the proximal end opening of the tool lumen 116. The shells 122 and 124 are coupled together through a coupling mechanism 128 as shown in FIGS. 7 and 9 that allows the cap 114 to be retracted proximally away from the handle shaft 112 as shown in FIGS. 6 and 7 or advanced distally over or into greater proximity with the handle shaft 112 as shown in FIGS. 8 and 9 in the manner of a collet mechanism, wherein the elastic gripping ring 130 acts as the collet.

For example, as the cap 114 is rotated about the shaft 112, the cap 114 is advanced distally towards the handle shaft 112 and against end wall 117 so that the cup-shaped interior space 126 is minimized, as shown in FIG. 9, causing the elastic gripping ring 130 to be compressed about a proximal portion 129 of the lead body 60 to grip the lead body 60 tightly and prevent rotation or axial movement of the lead body 60 with respect to the torque transfer sheath body 104 without lead body damage. The cup-shaped interior space 126 is maximized as the cap 114 is advanced proximally away from the handle shaft 112, as illustrated in FIG. 7, to allow the elastic gripping ring 130 to assume its uncompressed shape and release the proximal portion 129 of the lead body 60 to allow rotation or axial movement of the lead body 60 with respect to the torque transfer sheath body 104.

Advantageously, the elastic gripping ring 130 provides a hemostasis function to block leakage of fluids within the torque transfer sheath body lumen 106 at times during the implantation procedure that the elastic gripping ring 130 is compressed against the portion of lead body 60. Therefore, lead body 60 does not have to be advanced through a separate hemostasis valve.

The coupling mechanism 128 can include mating screw threads or a bayonet mechanism that enables tightening or loosening and axial movement of cap 114 with respect to handle shaft 112 by rotation of the cap 114. Or the coupling mechanism 128 can include mating splines or the like that enable a push-pull movement of cap 114 with respect to handle shaft 112. The cap 114 is depicted as being rotated to advance the cap 114 distally or retract the cap 114 proximally with respect to the handle shaft 112 simply for convenience of illustration.

In use, implantable cardiac lead 10 and the introducer system including the outer sheath 80 and the torque transfer tool 100 are assembled together in a sterile field outside the patient's body prior to implantation with the lead body 60 and sheaths 80 and 102 relatively straight. The outer sheath body 82 is shown schematically in FIGS. 10–12 to allow the torque transfer sheath body 104 and lead body 60 to be seen within the outer sheath lumen 84.

The lead body 60 is inserted through the torque transfer tool lumen 116 while cap 114 is in the position depicted in FIGS. 6 and 7, disposing the distal fixation helix 70 within the torque transfer sheath body lumen 106. The torque transfer sheath body distal end 108 is advanced through the septum 96, and then through the hub lumen 92 and the outer sheath body lumen 84. Advantageously, the lead body 60 is disposed within the torque transfer sheath lumen 106 and therefore is not in contact with the septum 96. The torque transfer sheath body 104 has sufficient pushability so that the torque transfer sheath body 104 can be advanced or retracted through the septum 96 with ease thereby enabling advancement of the cardiac lead body 60 distally.

The lead distal segment LDS of the cardiac lead body 60 is then advanced outward from the distal end 108 of the torque transfer sheath body 104 and disposed in the sheath distal segment SDS of the outer sheath lumen 84 extending between the outer and torque transfer sheath body distal ends 88 and 108. The distal fixation helix 70 is extended from the outer sheath distal end 88 by pushing on the lead body proximal segment LPS to expose the helical coil turns through approximately the helix length HL. The lead intermediate segment LIS of the cardiac lead body 60 is disposed within the torque transfer sheath body lumen 106 of the torque transfer sheath body 104 that is in turn disposed within the sheath proximal segment SPS of the outer sheath lumen 84. A proximal segment of the cardiac lead body 60 extends proximally from the outer sheath hub 90 and through the torque transfer tool lumen 116. The full length of the torque transfer sheath body 104 is disposed within the hub lumen 92 and the outer sheath body lumen 84 as shown in FIG. 10.

Turning to FIG. 11, once the lead body 60 is positioned within the torque transfer sheath body 104 of the torque transfer tool and the lead body 60 and torque transfer tool 100 are inserted within the outer sheath 80, the torque transfer handle 110 is then locked to the lead body 60 as described above with respect to FIGS. 8 and 9. The torque transfer tool 100 and lead 10 are then retracted proximally an axial translation distance including at least the fixation helix length HL sufficient to pull the lead body 60 proximally and retract the distal fixation helix 70 into the outer sheath lumen 84. The distance between the sheath body distal ends 88 and 108 is then equal to about SDS+HL as shown in FIG. 11. The physician can observe this retraction since the assembly is outside the patient's body.

The assembly of the introducer system and the cardiac lead 10 is then inserted through the skin incision and the transvenous pathway to dispose the outer sheath body distal end 88 at a desired implantation site of FIG. 1 or FIG. 2, for example. The torque transfer sheath length ISL of the torque transfer sheath body 104 is selected such that the distal segment SDS of the outer sheath body 82 is relatively straight when the desired implantation site is reached. The proximal segment SPS of the outer sheath body 82 is typically bent into multiple curves of the tortuous pathway. Most of the torque transfer sheath body 104 and the intermediate segment LIS of the cardiac lead body 60 are also disposed in the twists and turns of the tortuous pathway. But, the intermediate segment LIS is confined within the torque transfer sheath lumen 106 and stiffened by the torque transfer sheath body 104 to increase pushability and torque-ability of the lead body 60 through the twists and turns. While the lumen diameter of the outer sheath body 82 may change slightly under pressure in tight turns, the torque transfer sheath body 104 maintains a constant diameter torque transfer sheath lumen 106. The distal segment LDS of the lead body 60 can therefore be pushed distally within the outer sheath lumen 84 to eject the fixation helix 70 from the distal end 88 of the outer sheath body 82 by advancing the torque transfer handle 110 distally through the axial translation distance corresponding at least to the helix length HL as shown in FIG. 12.

The torque transfer handle 110 is still locked to the proximal portion 129 of the lead body, and the distal fixation helix 70 can then be rotated as shown in FIG. 12 to screw the distal fixation helix 70 into the cardiac tissue or vessel wall by simultaneous rotation of the lead body 60 and the torque transfer sheath body 104 through rotation of the proximal tool handle 110 in the proper direction. The torque is transferred through the torque transfer sheath body 104 and the intermediate segment LIS of the lead body 60 without substantial loss, but the distal segment LDS of the lead body 60 can wind up within the larger diameter distal segment SDS of the outer sheath lumen 84. It has been found that the requisite number of turns N of the fixation helix 70 can be repeatedly achieved by rotating the torque tool handle through N+X turns, where X is determined empirically for any given design and characteristics of the screw-in lead 10 and the introducer system. The torque tool handle 110 is marked by mark 134 so that the physician can count the N+X turns. The physician may also experience tactile feedback transmitted from the torque transfer sheath 102 as the torque transfer sheath distal end 108 rotates against the outer sheath wall and through each 360° turn particularly if the outer sheath body 82 is bent or curved in the pathway at or near the torque transfer sheath distal end 108.

Once the fixation helix 70 is properly positioned within the cardiac tissue or vessel wall, the torque transfer handle 110 is unlocked from the lead body 60 by advancing the cap 114 from the engaging position illustrated in FIG. 9 to non-engaging position shown in FIG. 7, and the introducer system including the outer sheath 80 and the torque transfer tool 100 is then retracted proximally over the lead body 60 if the thresholds and retention force are acceptable. Attachment may be verified by observing that the introducer system can be retracted proximally over the lead body without retracting the lead body itself or by observing lead motion under fluoroscopy. Pacing and sensing threshold measurements are made through the distal pace/sense electrode(s) in the manner well known in the art prior to or following retraction of the introducer system.

A further embodiment of the present invention combines the torque transfer tool with the outer sheath into a combined introducer system 150, the proximal portion of which is depicted in FIGS. 13–18. In the combined introducer system 150, the outer sheath proximal hub and the torque transfer handle are coupled together for selective rotational and axial adjustment between an unlocked and proximally retracted position or configuration depicted in FIGS. 13 and 14, a locked and distally extended position or configuration depicted in FIGS. 15 and 16, and a locked and proximally retracted position or configuration depicted in FIGS. 17 and 18, during certain of the steps illustrated in FIG. 27. The coupling mechanism governs the axial translation distance that the distal fixation helix 70 is advanced as well as the number of turns that the torque transfer tool is rotated in movement from the proximally retracted and distally extended configurations.

As illustrated in FIGS. 13–18, the introducer system according to the present invention includes a torque transfer tool 200 and an outer sheath 180. The torque transfer tool 200 includes a torque transfer tool hub body 193, extending from a threaded proximally extending portion 199 having mating threads 197 positioned thereon, to a connecting portion 190, and a torque transfer handle 210 that includes a handle cap 214 and a rotatable handle shaft 212, shown in greater detail in FIGS. 19–21. The outer sheath 180 and hub body 193 are attached together through the threaded interaction of mating threads 198 formed between the outer sheath 180 and the connecting portion 190 of the hub body 193. The outer sheath 180 further includes an outer sheath body 182 extending from an outer sheath hub body 191 and through a distally extending flex strain relief tube 195 to an outer sheath distal end 188 shown in FIGS. 13 and 14. The outer sheath body 182 can be formed of the same materials and have the dimensions of the outer sheath body 82, for example, as described above.

A hub lumen 192 extends axially through the lengths of the hub body 193 and the outer sheath hub body 191, and a branch of the hub lumen 192 extends through a side port 194 extending laterally from the hub body 193. The hub lumen 192 is axially aligned with and in fluid communication with an outer sheath body lumen 184 extending axially through the outer sheath body 182. The side port 194 can be coupled with an aspiration source or an infusion source and can be capped or include a valve that can be opened and closed to selectively provide aspiration or fluids from or infusion of fluids into the hub lumen 192 and the outer sheath body lumen 184 in a manner well known in the art. A flexible annular seal 196 is disposed within an annular groove of the hub lumen 192 within hub body 193. The annular seal 196 can take any form including a single O-ring, rib or wiper or the like, or may include a series of flexible annular ribs or wipers or the like arrayed along the hub lumen 192 proximal to the side port 194 that inhibits leakage of fluid in hub lumen 192 proximally.

The introducer system 150 of the present invention depicted in FIGS. 13–18 further includes an elongated torque transfer sheath 202 that is preferably formed of a torque transfer sheath body 204 including a length of thin walled tubing of the materials, characteristics and dimensions described above with respect to torque transfer sheath body 104 and that includes a torque transfer sheath body lumen 206 that extends axially through the torque transfer sheath body 204.

The diameter of the torque transfer sheath body lumen 206 is dependent upon the lead body diameter and the above-specified clearance, and the outer diameter of the torque transfer sheath body 204 is dependent upon these factors and twice the thickness of the wall of the torque transfer sheath body 204. The diameter of the outer sheath body lumen 184 is dependent upon the outer diameter of the torque transfer sheath body 204 and the specified clearance of the torque transfer sheath body 204 within the outer sheath body lumen 184. The diameter of the outer sheath body 182 is then dependent upon the diameter of the outer sheath body lumen 184 plus twice the wall thickness of the outer sheath body 182.

The torque transfer sheath body 204 is shorter in length than the outer sheath body 182 and is disposed to extend through the hub lumen 192 and the outer sheath body lumen 184 in the same manner as shown in FIGS. 10–12. The torque transfer sheath body 204 is movable between a distally advanced position that defines the distance between the sheath body distal ends, i.e., the sheath distal segment SDS shown in FIGS. 10 and 12, and a proximally retracted position as described further below. The torque transfer sheath body 204 extends through the hub lumen 192 and the lumen of the elastic annular seal 196 disposed within the hub lumen 192. Advantageously, the lead body 60 is disposed within the torque transfer sheath lumen 206 and therefore is not in contact with this elastic annular seal 196. The torque transfer sheath body 204 has sufficient pushability so that the torque transfer sheath body 204 can be advanced or retracted through the annulus of the elastic annular seal 196 with ease, as the torque transfer handle 210 and hub body 193 are adjusted between the locked and distally extended position of FIGS. 15 and 16 and the locked and proximally retracted position of FIGS. 17 and 18, thereby enabling advancement and retraction of the cardiac lead body 60 distally and proximally, respectively, as described below. In this way, the torque transfer sheath body 204 isolates the lead body 60 from the seal 196 and provides a sealing surface to inhibit leakage of fluid in hub lumen 192 proximally.

The torque transfer sheath body 204 extends within and is affixed to the handle shaft 212 along a proximal end 229 of the torque transfer sheath body 204, and the handle cap 214 is adjustably affixed to a proximal end of the handle shaft 212 through corresponding mating threads 228 located along a proximal portion 239 of the tubular handle shaft 212 and within handle cap 214, as shown in greater detail in FIGS. 19–21. The tubular handle shaft 212 is formed of a rigid thermoplastic material, for example, and has an axial bore 222 extending through the length of the handle shaft 212 from a proximal potion 211, an intermediate portion 225, to a distal portion 213. The distal portion 213 of the axial bore 222 is formed to receive the threaded proximally extending portion 199 of the hub body 193, and the proximal portion 211 of the axial bore 222 is formed to receive a ring-shaped elastic gripping ring 230.

Figure 14:
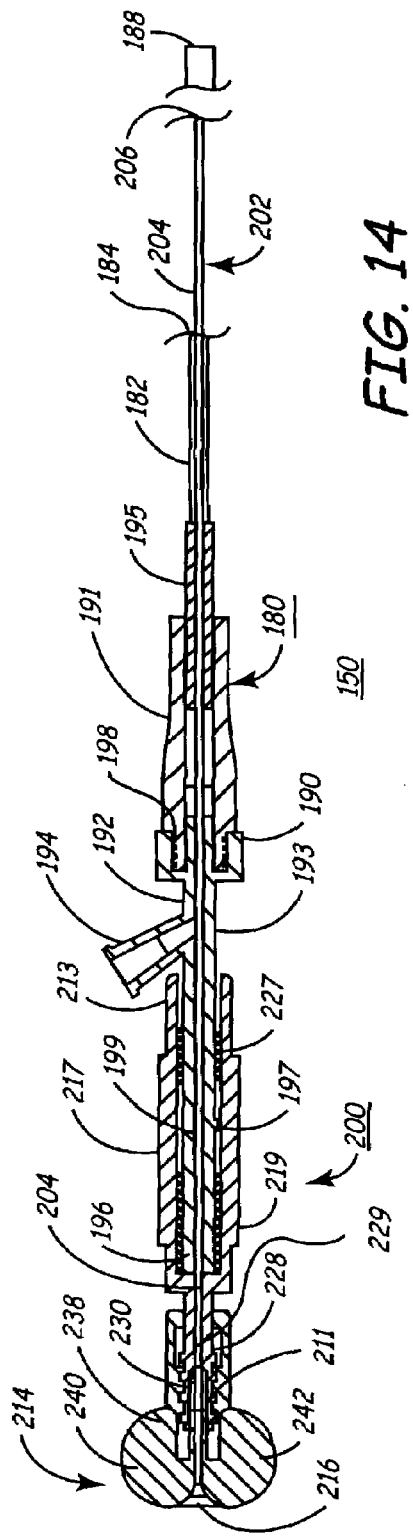
FIG. 14 is a cross-section view of the proximal portion of the combined torque transfer tool and outer sheath taken along line 14—14 of FIG. 13.

As illustrated in FIGS. 14, 16 and 18, the torque transfer sheath body 204 extends from the proximal end 229 positioned within the proximal portion 211 of the handle shaft 212, through the handle shaft 212, the hub body 193, the outer sheath hub 191, the strain relief tube 195, and within the outer sheath lumen 184 of outer sheath body, terminating proximal to the outer sheath distal end 188. A proximal segment of the torque transfer sheath body 204 is fixedly maintained within the axial bore 222 of the handle shaft 212 by adhesive applied along the intermediate portion 225 of the axial bore 222.

FIG. 22 is a schematic diagram of a torque tool hub body according to the present invention. As illustrated in FIG. 22, the hub body 193 includes a variable pitch outward extending spiral thread 197 that extends axially about the threaded proximally extending portion 199 of the hub body 193. The distal portion 213 of the handle shaft 212 is coupled to the proximal extending portion 199 of the hub body 193 through the interaction of the spiral thread 197 around the tubular proximal hub body 193 and an inwardly extending tooth 227 positioned along the handle shaft 212 extending inwardly to bear against and advance through grooves formed by the spiral thread 197 as the handle shaft 212 is rotated about the threaded proximally extending portion 199 of the hub body 193. Four gripping ribs 215, 217, 219, 221 (all shown in FIG. 21) are formed on the handle shaft 212 that facilitate application of torque to the handle shaft 212 to rotate and axially translate handle shaft 212 distally between the most proximal position shown in FIGS. 17 and 18 and the most distal position shown in FIGS. 13–16, respectively, in certain steps of the method of using the introducer system 150 described below with respect to FIG. 27.

Figure 23:
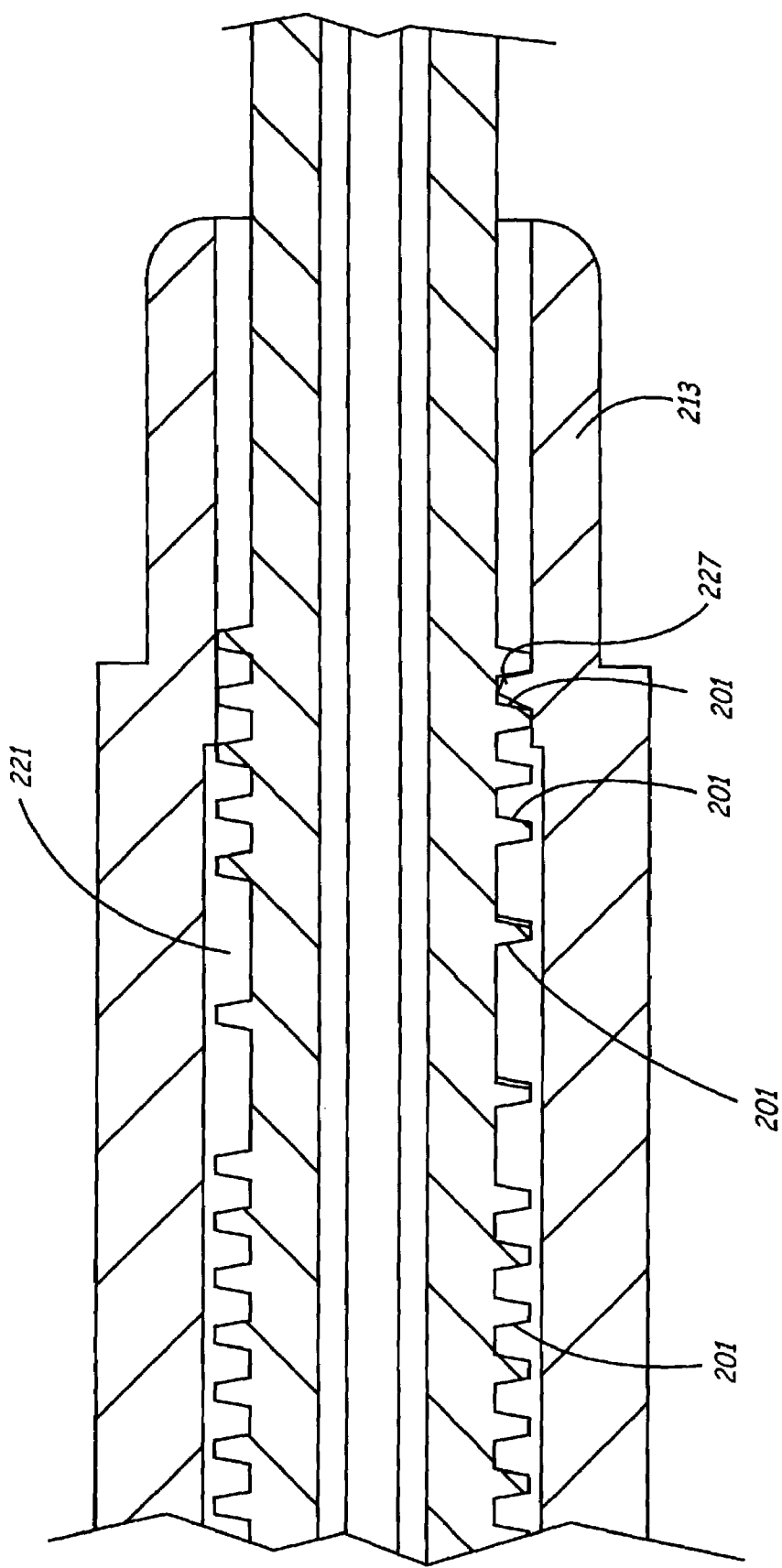
FIG. 23 is a cross-sectional view of a hub body and a tooth of a handle shaft of a torque transfer tool, according to the present invention, with the tooth of the handle shaft in an engaged position.

FIG. 23 is a cross-sectional view of the threaded proximally extending portion 199 of the hub body 193 positioned within the distal portion 213 with the tooth 227 in an engaged position. FIG. 24 is a cross-sectional view of the threaded proximally extending portion 199 of the hub body 193 positioned within the distal portion 213 with the tooth 227 in an non-engaged position. FIG. 25 is an end view of a tubular handle shaft of the present invention. According to the present invention, the handle shaft 212 is axially translated proximally without rotation from the most distal position shown in FIGS. 13–16 to the most proximal position shown in FIGS. 17 and 18 by pulling the handle shaft 212 proximally over the spiral thread 197 rather than rotating the tooth through the grooves formed by the spiral thread 197. In particular, as illustrated in FIGS. 20, 21 and 23–25, handle shaft 212 includes cut-out portions 250 that that form a narrow movable finger or cantilevered tab 223 cut that extends distally in the wall of the handle shaft 212 from a tab supported end 223a to a tab free end 223b. The tab free end 223b is in the engaged position shown in FIGS. 21 and 23, i.e., is deflected inward during rotation of the tool handle 210 during advancement of the tool handle 210 distally so that the inwardly extending tooth 227 is positioned within grooves 201 formed by spiral thread 197 and bears against and tracks the turns of the spiral thread 197. However, the inwardly extending tooth 227 includes an inclined portion 203 that enables the tab free end 223b of the cantilevered tab 223 to spring out so that the tab free end 223b is in the non-engaged position shown in FIGS. 24 and 25, i.e., the inwardly extending tooth 227 is extended outward from the spiral thread 197 so that the tooth 227 is no longer positioned within the grooves 201, and therefore the tooth 227 rides over the spiral thread 197 to allow the handle shaft 212 to be pulled proximally to the position shown in FIGS. 17 and 18 when force is applied to retract the tool handle 210 proximally away from the outer sheath 180, indicated by arrow A in FIG. 24, to retract the distal fixation helix 70 into the outer sheath lumen 184.

It is understood that while use a single tooth 227 is illustrated and described above, the present invention could include two or more teeth or other engaging members having corresponding inclined portions and positioned along tab 223 for engaging within grooves 201.

As illustrated in FIGS. 13–19, a tool lumen 216 extends through the handle shaft 212 and cap 214 in axial alignment with the torque transfer sheath body lumen 206 for insertion of the lead body 60 through the tool lumen 216 and the torque transfer sheath body lumen 206 in the same manner as shown in FIGS. 6–12. The tool lumen 216 is adapted to be selectively narrowed by rotating the cap 214 about the proximal portion 211 of the handle shaft 212 so that the tool handle 210 grips a portion of the lead body 60 using elastic gripping ring 230 to enable rotation of the torque transfer sheath body 204 and the lead body 60 within the torque transfer sheath body lumen 206 by rotation of the torque transfer cap 210 without damaging the lead body 60.

Figure 13:
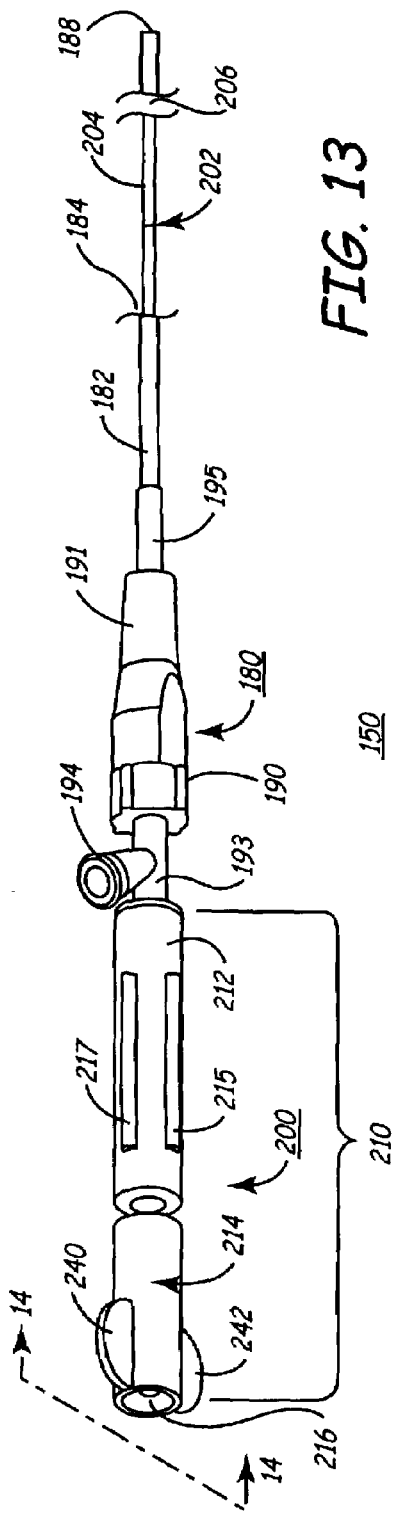
FIG. 13 is a plan view of the proximal portion of a further embodiment of the invention, wherein the torque transfer tool and the outer sheath are combined together into a combined introducer system and are depicted in the unlocked and distally extended configuration.

The handle cap 214 is formed of a rigid thermoplastic material and is shaped to define an interior cap bore 226 extending from a cap proximal end opening forming the proximal end opening of the tool lumen 216 that extends distally over the proximal end 211 of the handle shaft 212. The handle shaft 212 and the cap 214 are coupled together through coupling threads 228 that allows the cap 214 to be retracted proximally away from the handle shaft 212 as shown in FIGS. 13 and 14 or advanced distally over or into greater proximity with the handle shaft 212 as shown in FIGS. 15–18 by rotation of the cap 214. Wings 240 and 242 of cap 214 facilitate application of torque to the cap 214 to rotate and translate cap 214 distally or proximally with respect to the handle shaft 214.

Referring again to FIGS. 14,16, 18 and 19, the proximal portion 211 of the axial bore 222 at the proximal end 239 of the tubular handle shaft 212 is formed to receive and enclose the elastic gripping ring 230 that is disposed around the tool lumen 216 just proximal to the proximal end 229 of the torque transfer sheath body 204. The handle cap 214 is formed with a tubular plunger 238 extending distally having a plunger lumen defining the proximal portion of the tool lumen that bears against the proximal side of the elastic gripping ring 230. The elastic gripping ring 230 can be formed of elastic silicone rubber, or similar material that assumes the relaxed shape depicted in FIGS. 14 and 19 when not compressed enables free passage of the lead body 60 through the tool lumen 216 and the compressed shape depicted in FIGS. 16 and 18 when compressed longitudinally to firmly grip onto the lead body 60 extending through the gripping ring 230 to lock the lead 10 in place without damaging the lead body 60. The amount of force applied is controlled by the selection of the elastic gripping ring shape and properties as well as the number of turns that the cap 214 can be rotated. Again, the elastic gripping ring 230 functions as a hemostasis valve about the portion of the lead body 60 that it is compressed against so that fluids in the torque transfer sheath lumen 206 do not leak proximally.

According to the present invention, the spiral thread 197 of the hub body 193 is designed in conjunction with the torque transfer characteristics of any particular cardiac lead 10 used in a particular implementation of the introducer system 150 to compensate for the tendency of the lead body 60 to windup and resist rotation. As illustrated in FIG. 22, the spiral thread 197 includes a first portion 260 corresponding to a number, such as eight or nine, of closely spaced proximal torque preload turns, a second portion 261 corresponding to one or two elongated spiral translation turns, and a third portion 262 corresponding to a further number, such as five or six, of closely spaced distal screw-in fixation turns that govern the fixation of the fixation helix 70 into cardiac tissue. The distal fixation helix 70 is located within the distal end of the outer sheath lumen 184 when the cardiac lead 10 is loaded into and locked by the introducer system 150 as described further below. Thus, the first portion 260 of the spiral thread 197 includes a first selected number of thread turns or preload turns having a pitch selected to overcome windup of the lead body 60 within the outer sheath lumen 184 resisting transfer of rotational torque to the distal fixation helix 70, the second portion 261 of the spiral thread 197 includes a second number of thread turns selected in pitch and number to govern distal advancement of the torque transfer tool handle 210 with respect to the outer sheath 180 through the axial translation distance to eject the distal fixation helix 70 from the outer sheath lumen 184, and the third portion 262 of the spiral thread 197 includes a third number of thread turns selected to effect rotation of the distal fixation helix 70 to screw the distal fixation helix 70 into cardiac tissue.

The outer sheath body distal end 188 shown in FIG. 13 is advanced to the implantation site, and the handle 210 is rotated to with respect to the hub body 193 so that the handle shaft 212 rotates and moves distally, tracking the turns of the spiral thread 197. This rotation and distal movement of the handle shaft 212 in turn rotates and distally advances the torque transfer sheath 202 and the lead 60 through the outer sheath 180. The lead body 60 is rotated through the preload turns of the first portion 260 of the spiral thread 193 to build up torsion in the lead body 60 without moving the helix 70 appreciably distally. The handle 210 both rotates and advances distally over the widely spaced turn corresponding to the second portion 261 of the threaded helix 197 to cause the fixation helix 70 to be distally advanced or ejected from the outer sheath lumen 184 through the translation distance. Further rotation of the handle 210 over the closely spaced turns corresponding to the third portion 262 of the spiral thread 197 causes the fixation helix to rotate and fixate or screw into tissue. The number of turns is selected so that the fixation helix 70 is fully screwed in, but is not over rotated. In this particular example, most of the rotations of the handle 210 with respect to the hub body 193 are ineffectual to rotate the fixation helix due to the low ability of the lead body to transmit torque down its length even when assisted by the confining torque transfer sheath body 202. Thus, the torque transfer sheath body 204 can be moved distally within the outer sheath body lumen 184 through the axial translation distance. The axial translation distance exceeds the helix length HL in this embodiment, to be certain that the lead body 60 within the torque transfer sheath body lumen 206 can be moved distally to eject distal fixation helix 70 of lead 10 from the outer sheath distal segment SDS when the handle shaft 212 is moved distally to the most distal position shown in FIGS. 13–16.

Thus, the coupling mechanism including the inwardly extending tooth 227 and the pitch and number of turns of the spiral thread 197 govern the axial translation distance that the distal fixation helix 70 is advanced or retracted as well as the number of turns that the torque transfer tool 200 is rotated in movement from the proximally retracted and distally extended positions or configurations. Distal advancement and rotation of the distal fixation helix 70 advantageously occur simultaneously as the handle shaft 212 is rotated. The axial translation distance and number of rotations of the distal fixation helix can be established empirically for the particular characteristics of the cardiac lead body, the fixation helix, and the implantation site.

FIG. 26 is a cross-sectional view of a torque transfer tool according to an alternate embodiment of the present invention. It is understood that although the torque transfer sheath body has been described above as being shorter in length than the outer sheath body, and further that the length preferably corresponds to the length of the sheath proximal segment of the outer sheath lumen, it is understood that the torque transfer sheath body of the present invention is not intended to be limited to the length described above, but rather could include other lengths as desired, depending upon specific applications and types of leads involved. For example, as illustrated in FIG. 26 and as described in the embodiments above, the torque transfer sheath body 204 extends within and is affixed to the handle shaft 212 along the proximal end 229 of the torque transfer sheath body 204. However, the torque transfer sheath 202 in an alternate embodiment of the present invention of FIG. 26 differs from the torque transfer sheath 202 as described above in that the torque transfer sheath body 204 of the alternate embodiment extends from the proximal end 229 positioned within the proximal portion 211 of the handle shaft 212 to a torque transfer sheath body distal end 308 which is positioned within the handle shaft 212 and the hub body 193, rather than within the outer sheath lumen 184 of the outer sheath 180. In the same way as described above, the proximal segment of the torque transfer sheath body 204 is fixedly maintained within the axial bore 222 of the handle shaft 212 by adhesive applied along the intermediate portion 225 of the axial bore 222. Such an arrangement as illustrated by the embodiment of the present invention illustrated in FIG. 26 could be utilized, for instance, in situations where a larger diameter lead possessing physical characteristics that give the lead the required amount of torqueability and pushable so that it is no longer necessary for the torque transfer sheath 202 to provide those characteristics. In addition, depending upon the characteristics of the leads and type of introduction involved, the torque transfer sheath body distal end 308 could be positioned along any location within the handle shaft 212, hub body 193 and the outer sheath 180 of the torque transfer tool 200 of the present invention.

In addition, as illustrated in FIG. 26, once the handle shaft 212 is fully advanced distally so that the fixation helix 70 is fully engaged with the cardiac tissue or vessel, further rotation of the handle shaft 212 in the distal direction is prevented by abutting stop tabs 310 and 312 to prevent over rotation of the lead body 60 and fixation helix 70.

Figure 27:
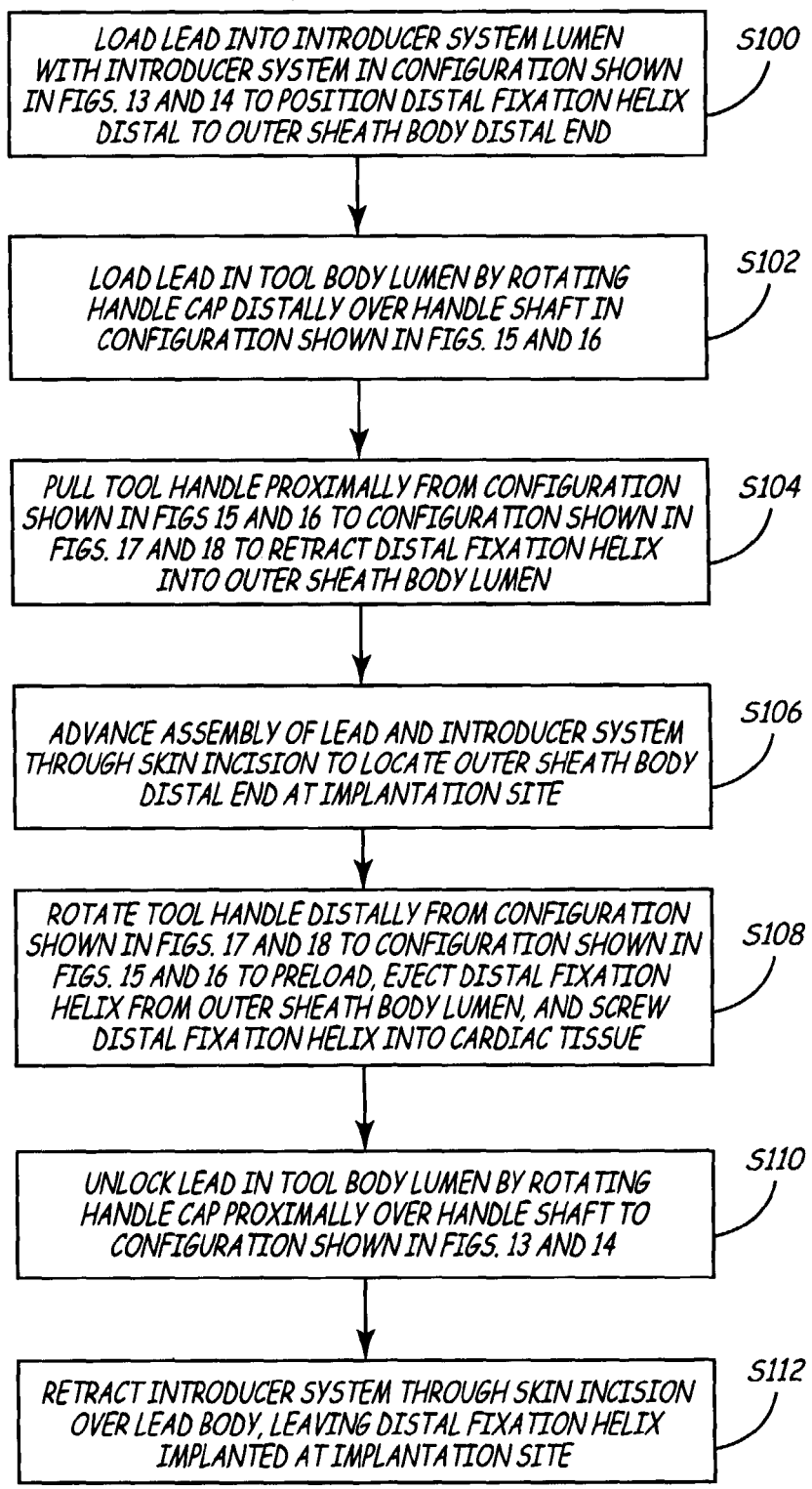
FIG. 27 is a flow chart illustrating steps of surgically implanting a cardiac lead employing he combined introducer system.

Preferred steps of using the torque transfer tool and introducer system of the present invention are depicted in FIG. 27. In step S100, the introducer system is disposed in the configuration depicted in FIGS. 13 and 14. The lead 10 is loaded into the introducer system lumen 116, 216 to extend through the torque transfer sheath lumen 106, 206 and the sheath distal segment SDS of outer sheath lumen to dispose a portion of lead body within the lumen of the elastic gripping ring 230 and to dispose the distal fixation helix 70 extending distally from the outer sheath distal end 188. In step S102, the handle cap 214 is rotated to be advanced from the non-engaging position or configuration shown in FIGS. 13 and 14 to the engaging position shown in FIGS. 15 and 16 to fixedly position the lead body 60 within the torque transfer tool 100, 200, as described above. The tool handle 210 is then pulled proximally with respect to the outer sheath hub 190 from the position or configuration shown in FIGS. 15 and 16 into the position shown in FIGS. 17 and 18 to simultaneously retract the lead body 60 and the torque transfer sheath 102, 202 within the outer sheath body 88, 108. The distal fixation helix 70 is thereby pulled into the outer sheath distal segment SDS proximal to the outer sheath body distal end 188 in the manner shown in FIG. 11.

The assembly of the lead and introducer system 150 is then introduced in step S106 through the skin incision and pathway, e.g., a pathway shown in FIG. 1 into the right heart chamber or FIG. 2 into the coronary sinus and a cardiac vein or even a trans-thoracic pathway to the epicardium of the heart to dispose the outer sheath body distal end 188 at the desired implantation site. The side port 194 is coupled to a vacuum source for aspiration and/or an irrigation source for irrigation.

In step S108, the tool handle 210 is then rotated and advanced distally from the position or configuration depicted in FIGS. 17 and 18 over the outer sheath hub 190 to the position or configuration depicted in FIGS. 15 and 16 to preload torque in the lead body, eject the distal fixation mechanism 70 from the outer sheath body lumen 188, and then screw the distal fixation helix 70 into cardiac tissue at the implantation site, as described above. Since the torque transfer sheath 102, 202 is fixedly positioned within handle shaft 112 and the hub body 193, respectively, and the lead body 60 is fixedly engaged within the torque transfer tool 100, 200 by the cap 114, 214 as described above, the advancement of the tool handle 110, 210 simultaneously rotates and advances both the lead body 60 and the torque transfer sheath 102, 202 within the outer sheath body 82, 182.

Advantageously, the physician need not count the number of turns, and the distal fixation helix 70 is screwed the requisite number of turns into the tissue without over rotating or coring the tissue. In the embodiment of the present invention illustrated in FIGS. 13–18, the physician need not remember to preload torque in the lead body 60 as is necessary in practicing the embodiment of the present invention illustrated in FIGS. 6–9. The distal fixation helix 70 is both advanced through the axial translation distance and screwed into the cardiac tissue in a single action in step S108 that is limited and governed by the pitch and number of turns of the spiral thread 197 to ensure consistent fixation at the implantation site.

The handle cap 214 is rotated in step S110 in the unlocking direction from the configuration depicted in FIGS. 15 and 16 to the configuration depicted in FIGS. 13 and 14 to decompress the elastic locking ring 230 and release the lead body 60 within the tool lumen 116, 216. The introducer system 150 can then be withdrawn over the lead body in step S112.

Pacing and sensing threshold measurements are determined before or after step S112, and the distal fixation helix 70 can be unscrewed and repositioned if the measurements are not acceptable. The lead proximal end connector assembly is routed to the implantation site of the IPG or monitor to be implanted. The lead proximal end is coupled with the IPG or monitor, and the IPG or monitor is subcutaneously implanted in the conventional manner.

All patents and publications identified herein are incorporated herein by reference in their entireties.

While particular embodiments of the invention have been disclosed herein in detail, this has been done for the purposes of illustration only, and is not intended to limit the scope of the invention as defined in the claims that follow. It is to be understood that various substitutions, alterations, or modifications can be made to the disclosed embodiment without departing from the spirit and scope of the claims. The above described implementations are simply those presently preferred or contemplated by the inventors, and are not to be taken as limiting the present invention to the disclosed embodiments. It is therefore to be understood, that within the scope of the appended claims, the invention may be practiced otherwise than as specifically described without actually departing from the spirit and scope of the present invention.

We claim:

1. An introducer system for positioning and fixedly engaging a distal fixation helix of a lead at an implantation site within a patient's body, comprising:
a torque transfer sheath, extending from a proximal end to a distal end, receiving the lead;
an outer sheath, having a distal end, receiving the lead positioned within the torque transfer sheath;
a handle operable between a first handle position enabling advancement and retraction of the lead through the handle and a second handle position fixedly engaging a proximal end of the lead within the handle, wherein the lead is advanced through the outer sheath to extend outward a predetermined distance from the distal end of the outer sheath and the fixation helix is rotated through the predetermined distance to be fixedly engaged at the implantation site in response to simultaneous rotation and advancement of the lead and the torque transfer sheath through rotation and advancement of the handle in the second handle position;
a hub body, extending from a proximally extending portion having a threaded portion positioned thereon to a connecting portion, the outer sheath and the hub body being fixedly engaged through threaded interaction of mating threads formed between the outer sheath and the connecting portion of the hub body;
a handle shaft having an axial bore extending through the length of the handle shaft from a proximal portion, to an intermediate portion, to a distal portion, the distal portion of the axial bore formed to receive the proximally extending portion of the hub body;
a first engaging member positioned within the distal portion of the axial bore advancing through grooves formed by the threaded portion of the hub body to distally advance the handle shaft when the handle is in the second handle position as the handle shaft is rotated about the proximally extending portion;
a second engaging member positioned within the proximal portion of the axial bore; and
a cap that is advanced distally towards the handle shaft to engage the second engaging member against the lead in response to the handle being in the second handle position and is retracted proximally from the handle shaft to disengage the second engaging member from the lead in response to the handle being in the first handle position, wherein the proximal end of the torque transfer sheath is fixedly positioned within the proximal portion of the handle shaft and the rotation of the handle shaft about the proximally extending portion of the hub body when the handle is in the second handle position transmits torque through the torque transfer sheath to the lead to screw the fixation helix extending from the distal end of the outer sheath body into the implantation site,
wherein the threaded portion includes a first portion having a first pitch and number of turns, a second portion having a second pitch and number of turns, and a third portion having a third pitch and number of turns, wherein the first portion, the second portion and the third portion correspond to torque transfer characteristics of the lead,
wherein the first pitch and number of turns is selected to overcome windup of the lead within the outer sheath resisting transfer of rotational torque to the fixation helix, the second pitch and number of turns is selected to govern distal advancement of the fixation helix from the distal end of the outer sheath, and the third pitch and number of turns is selected to effect rotation of the fixation helix to engagte the fixation helix at the implantation site.

2. The introducer system of claim 1, further comprising a seal member sealably inhibiting leakage of fluid proximally through the torque transfer sheath.

3. The introducer system of claim 2, wherein the handle includes a handle shaft and a cap, the cap capable of being positioned axially along the handle shaft between a first cap position, corresponding to the seal member not being sealably engaged against the lead and the handle being in the first handle position, and a second cap position, corresponding to the seal member being sealable engaged against the lead and the handle being in the second handle position.

4. The introducer system of claim 2, wherein the torque transfer sheath extends through the seal member and is sealably advanced through the seal member during rotation and advancement of the handle operated in the second handle position.

5. The introducer system of claim 1, further comprising means for controlling the rotation and advancement of the handle in the second position to advance the fixation helix to extend outward the predetermined distance from the distal end of the outer sheath and to rotate the fixation helix a predetermined number of turns at the implantation site.

6. An introducer system for positioning and fixedly engaging a distal fixation helix of a lead at an implantation site within a patient's body, comprising:
a torque transfer sheath, extending from a proximal end to a distal end, receiving the lead;
an outer sheath, having a distal end, receiving the lead positioned within the torque transfer sheath;
a handle operable between a first handle position enabling advancement and retraction of the lead through the handle and a second handle position fixedly engaging a proximal end of the lead within the handle, wherein the lead is advanced through the outer sheath to extend outward a predetermined distance from the distal end of the outer sheath and the fixation helix is rotated through the predetermined distance to be fixedly engaged at the implantation site in response to simultaneous rotation and advancement of the lead and the torque transfer sheath through rotation and advancement of the handle in the second handle position; a hub body, extending from a proximally extending portion having a threaded portion positioned thereon to a connecting portion, the outer sheath and the hub body being fixedly engaged through threaded interaction of mating threads formed between the outer sheath and the connecting portion of the hub body;
a handle shaft having an axial bore extending through the length of the handle shaft from a proximal portion, to an intermediate portion, to a distal portion, the distal portion of the axial bore formed to receive the proximally extending portion of the hub body;
a first engaging member positioned within the distal portion of the axial bore advancing through grooves formed by the threaded portion of the hub body to distally advance the handle shaft when the handle is in the second handle position as the handle shaft is rotated about the proximally extending portion;
a second engaging member positioned within the proximal portion of the axial bore; and
a cap that is advanced distally towards the handle shaft to engage the second engaging member against the lead in response to the handle being in the second handle position and is retracted proximally from the handle shaft to disengage the second engaging member from the lead in response to the handle being in the first handle position, wherein the proximal end of the torque transfer sheath is fixedly positioned within the proximal portion of the handle shaft and the rotation of the handle shaft about the proximally extending portion of the hub body when the handle is in the second handle position transmits torque through the torque transfer sheath to the lead to screw the fixation helix extending from the distal end of the outer sheath body into the implantation site, wherein, once the handle is in the second handle position, the handle shaft is rotated about the proximally extending portion to advance the handle shaft between a proximally retracted position corresponding to the fixation helix being positioned within the outer sheath and a distally extended position corresponding to the fixation helix being fully extended from the distal end of the outer sheath, and wherein the first engaging member is axially translated across the threaded portion as the handle shaft is advanced from the distally extended position to the proximally retracted position.

7. The introducer system of claim 1, wherein, once the handle is in the second handle position, the handle shaft is rotated about the proximally extending portion to advance the handle shaft between a proximally retracted position corresponding to the fixation helix being positioned within the outer sheath and a distally extended position corresponding to the fixation helix being fully extended from the distal end of the outer sheath, wherein the first engaging member includes an inclined portion and the handle shaft includes a cantilevered tab extending distally along the handle shaft from a tab supported end to a tab free end, wherein the tab free end is deflected inward so that the first engaging member is positioned within the grooves formed by thread portion during rotation of the handle shaft during advancement of the handle shaft from the proximally retracted position to the distally extended position, and the inclined portion deflects the tab free end outward from the threaded portion so that the first engaging member is not positioned within the threaded portion and the first engaging member is axially translated across the threaded portion as the handle shaft is advanced from the distally extended position to the proximally retracted position.

8. The introducer system of claim 1, wherein the distal end of the torque transfer sheath is positioned within the outer sheath.

9. The introducer system of claim 1, wherein the distal end of the torque transfer sheath is positioned within the handle.

10. An introducer system for positioning and fixedly engaging a distal fixation helix of a lead at an implantation site within a patient's body, comprising:

a torque transfer sheath, extending from a proximal end to a distal end, receiving the lead;

an outer sheath, having a distal end, receiving the lead positioned within the torque transfer sheath;

a hub body, extending from a proximally extending portion having a threaded portion positioned thereon to a connecting portion, the outer sheath and the hub body being fixedly engaged through threaded interaction of mating threads formed between the outer sheath and the connecting portion of the hub body;

a handle shaft having an axial bore extending through the length of the handle shaft from a proximal portion to a distal portion, the distal portion of the axial bore formed to receive the proximally extending portion of the hub body;

a first engaging member positioned within the proximal portion of the axial bore;

a cap that is advanced distally towards the handle shaft to engage the first engaging member against the lead to position the cap in a first cap position fixedly engaging the lead within the handle shaft and is retracted proximally from the handle shaft to disengage the second engaging member from the lead to position the cap in a second cap position enabling advancement of the lead through the handle shaft; and a second engaging member positioned within the distal portion of the axial bore and advancing through grooves formed by the threaded portion of the hub body to distally advance the handle shaft when the cap is in the first cap position as the handle shaft is rotated about the proximally extending portion, wherein the proximal end of the torque transfer sheath is fixedly positioned within the proximal portion of the handle shaft and the rotation of the handle shaft about the proximally extending portion of the hub body when the cap is in the first cap position transmits torque through the torque transfer sheath to the lead to screw the fixation helix extending from the distal end of the outer sheath body into the implantation site, wherein, once the handle is in the second handle position, the handle shaft is rotated about the proximally extending portion to advance the handle shaft between a proximally retracted position corresponding to the fixation helix being positioned within the outer sheath and a distally extended position corresponding to the fixation helix being fully extended from the distal end of the outer sheath, wherein the second engaging member includes an inclined portion and the handle shaft includes a cantilevered tab extending distally along the handle shaft from a tab supported end to a tab free end, wherein the tab free end is deflected inward so that the second engaging member is positioned within the grooves formed by thread portion during rotation of the handle shaft during advancement of the handle shaft from the proximally retracted position to the distally extended position, and the inclined portion deflects the tab free end outward from the threaded portion so that the second engaging member is not positioned within the threaded portion and the second engaging member is axially translated across the threaded portion as the handle shaft is advanced from the distally extended position to the proximally retracted position.

11. The introducer system of claim 10, further comprising a seal member sealably inhibiting leakage of fluid proximally through torque transfer sheath, wherein the torque transfer sheath extends through the seal member and is sealably advanced through the seal member during rotation and advancement of the handle shaft when the cap is in the first cap position.

12. The introducer system of claim 10, further comprising means for controlling the rotation and advancement of the handle when the cap is in the first cap position to advance the rotation helix to extend outward a predetermined distance from the distal end of the outer sheath and to rotate the fixation helix a predetermined number of turns at the implantation site.

13. The introducer system of claim 10, wherein, once the handle is in the second handle position, the handle shaft is rotated about the proximally extending portion to advance the handle shaft between a proximally retracted position corresponding to the fixation helix being positioned within the outer sheath and a distally extended position corresponding to the fixation helix being fully extended from the distal end of the outer sheath, and wherein the second engaging member is axially translated across the threaded portion as the handle shaft is advanced from the distally extended position to the proximally retracted position.

14. The introducer system of claim 10, wherein the distal end of the torque transfer sheath is positioned within the outer sheath.

15. The introducer system of claim 10, wherein the distal end of the torque transfer sheath is positioned within the handle.

16. An introducer system for positioning and fixedly engaging a distal fixation helix of a lead at an implantation site within a patient's body, comprising:
   a torque transfer sheath, extending from a proximal end to a distal end, receiving the lead;
   an outer sheath, having a distal end, receiving the lead positioned within the torque transfer sheath;
   a hub body, extending from a proximally extending portion having a threaded portion positioned thereon to a connecting portion, the outer sheath and the hub body being fixedly engaged through threaded interaction of mating threads formed between the outer sheath and the connecting portion of the hub body;
   a handle shaft having an axial bore extending through the length of the handle shaft from a proximal portion to a distal portion, the distal portion of the axial bore formed to receive the proximally extending portion of the hub body;
   a first engaging member positioned within the proximal portion of the axial bore;
   a cap that is advanced distally towards the handle shaft to engage the first engaging member against the lead to position the care in a first care position fixedly engaging the lead within the handle shaft and is retracted proximally from the handle shaft to disengage the second engaging member from the lead to position the cap in a second cap position enabling advancement of the lead through the handle shaft; and
   a second engaging member positioned within the distal portion of the axial bore and advancing through grooves formed by the threaded portion of the hub body to distally advance the handle shaft when the cap is in the first cap position as the handle shaft is rotated about the proximally extending portion,
   wherein the proximal end of the torque transfer sheath is fixedly positioned within the proximal portion of the handle shaft and the rotation of the handle shaft about the proximally extending portion of the hub body when the cap is in the first cap position transmits torque through the torque transfer sheath to the lead to screw the fixation helix extending from the distal end of the outer sheath body into the implantation site;
   wherein the threaded portion includes a first portion having a first pitch and number of turns, a second portion having a second pitch and number of turns, and a third portion having a third pitch and number of turns, wherein the first portion, the second portion and the third portion correspond to torque transfer characteristics of the lead,
   wherein the first pitch and number of turns is selected to overcome windup of the lead within the outer sheath resisting transfer of rotational torque to the fixation helix, the second pitch and number of turns is selected to govern distal advancement of the fixation helix from the distal end of the outer sheath, and the third pitch and number of turns is selected to effect rotation of the fixation helix engage the fixation helix at the implantation site.

17. A method for positioning and fixedly engaging a distal fixation helix of a lead at an implantation site within a patient's body, comprising the steps of:
   inserting a lead through a handle and a torque transfer sheath while the handle is in a first handle position enabling advancement and retraction of the lead through the handle and extending a distal fixation helix of the lead outward a predetermined distance from an outer sheath distal end;
   fixedly engaging the lead body within the handle;
   retracting the lead and the torque transfer sheath within the outer sheath to advance the fixation helix within the outer sheath;
   positioning the outer sheath at the implantation site; and
   rotating the handle to rotate and advance the lead and the torque transfer sheath simultaneously through the outer sheath to extend the fixation helix outward a predetermined distance from the end of the outer sheath and to rotate the fixation helix through the predetermined distance to be fixedly engaged at the implantation site,
   advancing an engaging member through a first portion of a threaded portion having a first pitch and number of turns, a second portion having a second pitch and number of turns, and a third portion having a third pitch and number of turns, wherein the first portion, the second portion and the third portion correspond to torque transfer characteristics of the lead; and
   axially translating the engaging member across the threaded portion as the handle is advanced from a distally extended position corresponding to the fixation helix being fully extended from the distal end of the outer sheath to a proximally retracted position corresponding to the fixation helix being positioned within the outer sheath.

18. The method of claim 17, wherein the step of rotating further comprises controlling the rotation of the handle to advance the fixation helix to extend outward the predetermined distance from the distal end of the outer sheath and rotate the fixation helix a predetermined number of turns at the implantation site.

* * * * *

UNITED STATES PATENT AND TRADEMARK OFFICE
CERTIFICATE OF CORRECTION

| | |
|---|---|
| PATENT NO. | : 7,158,838 B2 |
| APPLICATION NO. | : 10/356143 |
| DATED | : January 2, 2007 |
| INVENTOR(S) | : Seifert et al. |

It is certified that error appears in the above-identified patent and that said Letters Patent is hereby corrected as shown below:

In column 27, line 37, please replace "first care position" with --first cap position--.

In column 28, line 29, please replace "site; and rotating" with --site; rotating--.

Signed and Sealed this

Second Day of October, 2007

JON W. DUDAS
*Director of the United States Patent and Trademark Office*